US012584099B2

(12) United States Patent
Faraghiparapari et al.

(10) Patent No.: US 12,584,099 B2
(45) Date of Patent: *Mar. 24, 2026

(54) METHOD FOR PREPARING CULTURES OF LACTIC ACID BACTERIA

(71) Applicant: Chr. Hansen A/S, Hoersholm (DK)

(72) Inventors: Neda Faraghiparapari, Hoersholm (DK); Marie Penderup Jensen, Hoersholm (DK); Jakub Kovacs, Hoersholm (DK); Anisha Goel, Hoersholm (DK)

(73) Assignee: Chr. Hansen A/S, Hoersholm (DK)

( * ) Notice: Subject to any disclaimer, the term of this patent is extended or adjusted under 35 U.S.C. 154(b) by 0 days.

This patent is subject to a terminal disclaimer.

(21) Appl. No.: 18/654,969

(22) Filed: May 3, 2024

(65) Prior Publication Data

US 2024/0368532 A1     Nov. 7, 2024

Related U.S. Application Data

(62) Division of application No. 17/784,055, filed as application No. PCT/EP2020/085582 on Dec. 10, 2020, now Pat. No. 11,981,890.

(30) Foreign Application Priority Data

Dec. 10, 2019     (EP) ..................................... 19214892

(51) Int. Cl.
| | |
|---|---|
| *C12N 1/20* | (2006.01) |
| *A23C 19/06* | (2006.01) |
| *A23K 10/16* | (2016.01) |
| *A23L 33/145* | (2016.01) |
| *C12N 1/16* | (2006.01) |
| *C12N 1/165* | (2026.01) |
| *C12N 1/18* | (2006.01) |
| *C12N 1/185* | (2026.01) |
| *C12R 1/645* | (2006.01) |
| *C12R 1/865* | (2006.01) |

(52) U.S. Cl.
CPC .............. *C12N 1/20* (2013.01); *A23C 19/061* (2013.01); *A23K 10/16* (2016.05); *A23L 33/145* (2016.08); *C12N 1/165* (2021.05); *C12N 1/185* (2021.05); *A23V 2002/00* (2013.01); *C12N 2500/98* (2013.01); *C12R 2001/645* (2021.05); *C12R 2001/865* (2021.05)

(58) Field of Classification Search
CPC .......... C12N 1/20; C12N 1/165; C12N 1/185; C12N 2500/98; C12N 1/145; C12N 1/38; A23C 19/061; A23K 10/16; A23L 33/145; A23V 2002/00; C12R 2001/645; C12R 2001/865
See application file for complete search history.

(56) References Cited

U.S. PATENT DOCUMENTS

| | | | |
|---|---|---|---|
| 10,779,743 | B2 | 9/2020 | Van Dam et al. |
| 11,172,860 | B2 | 11/2021 | Van Dam et al. |
| 11,981,890 | B2 | 5/2024 | Faraghiparapari et al. |
| 2002/0034815 | A1 | 3/2002 | Blank et al. |
| 2019/0200658 | A1 | 7/2019 | Vrljic et al. |

FOREIGN PATENT DOCUMENTS

| | | |
|---|---|---|
| CN | 101137745 A | 3/2008 |
| WO | WO-2005/003327 | 1/2005 |
| WO | WO-2014/029758 A1 | 2/2014 |
| WO | WO-2015/063282 A1 | 5/2015 |

OTHER PUBLICATIONS

Cheirsilp, Benjamas et al.; "Enhanced kefiran production by mixed culture of Lactobacillus kefiranofaciens and *Saccharomyces cerevisiae*"; Journal of Biotechnology, vol. 100, No. 1; Jan. 2003; pp. 43-53.

Cheirsilp, Benjamas et al.; "Interactions between Lactobacillus kefiranofaciens and *Saccharomyces cerevisiae* in Mixed Culture for Kefiran Production"; Journal of Bioscience and Bioengineering, vol. 96, No. 3; Dec. 17, 2003; pp. 279-284.

Lechardeur, Delphine et al.; "Using heme as an energy boost for lactic acid bacteria"; Current Opinion in Biotechnology, vol. 22; Jan. 4, 2011; pp. 143-149.

Mogensen, G et al.; "Inventory of Microorganisms with a Documented History of Use in Food"; (with abstract); Bulletin of the International Dairy Federation, 377; Jan. 2002; pp. 10-19.

Pedersen, Martin et al.; "Aerobic Respiration Metabolism in Lactic Acid Bacteria and Uses in Biotechnology"; Annual Review of Food Science and Technology, vol. 3; Nov. 7, 2011; pp. 37-58.

Prado, Maria R. et al.; "Milk kefir: composition, microbial cultures, biological activities, and related products"; Frontiers in Microbiology, vol. 6; Oct. 30, 2015; pp. 10 pages.

Yamasaki-Yashiki, Shino et al.; "Analysis of gene expression profiles of Lactobacillus paracasei induced by direct contact with *Saccharomyces cerevisiae* through recognition of yeast mannan"; Bioscience of Microbiota, Food and Health, vol. 36(1); Nov. 12, 2016; pp. 17-25.

Zheng, Jinshui et al.; "A taxonomic note on the genus Lactobacillus: Description of 23 novel genera, emended description of the genus Lactobacillus Beijerinck 1901, and union of Lactobacilliau and Leuconostocaceae"; Int J Syst Evol Microbiol 70(4); Apr. 2020; 155 pages.

Zotta, T. et al.; "Aerobic metabolism in the genus Lactobacillus: impact on stress response and potential applications in the food industry"; Journal of Applied Microbiology, vol. 122, vol. 4; Feb. 16, 2017; pp. 857-869.

*Primary Examiner* — Kade Ariani
(74) *Attorney, Agent, or Firm* — Eric J. Fechter

(57) ABSTRACT

Microbial starter cultures. More specifically, a method for preparing a microbial culture such as a lactic acid bacteria (LAB) starter culture wherein at least one microbial strain such as a lactic acid bacteria and at least one inactivated yeast strain is inoculated in a culture medium.

10 Claims, 13 Drawing Sheets

METHOD FOR PREPARING CULTURES OF LACTIC ACID BACTERIA

CROSS-REFERENCE TO RELATED APPLICATIONS

Figure 1A:
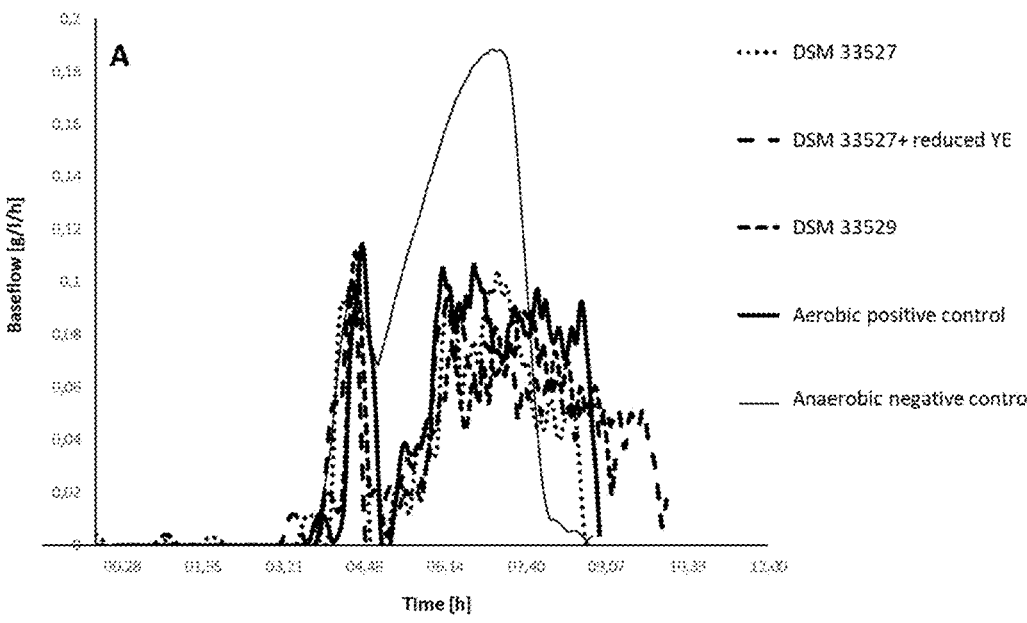
Figure 1B:
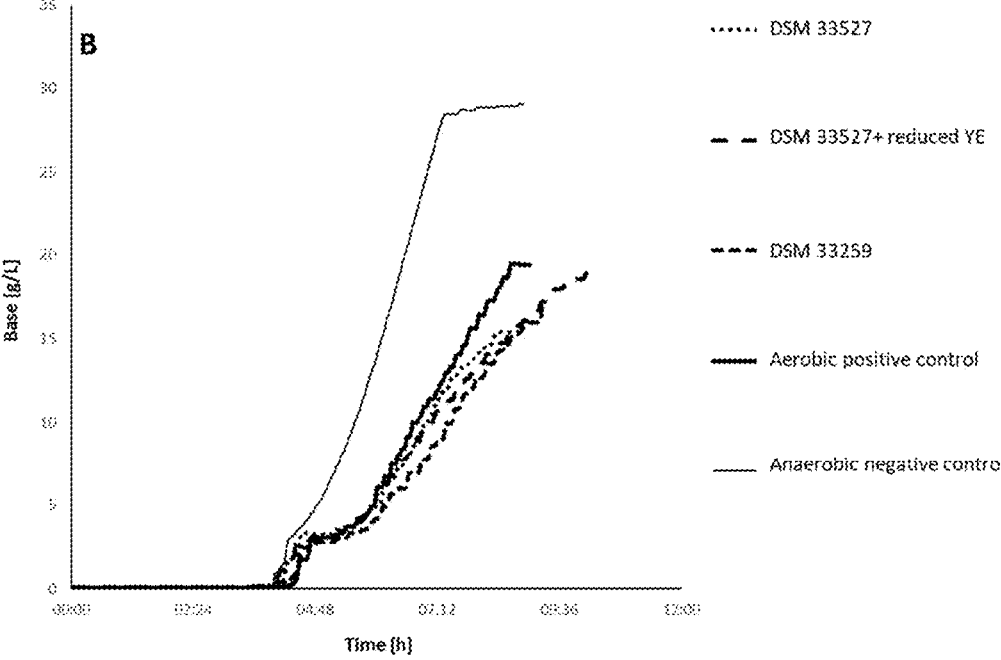
Figure 1C:
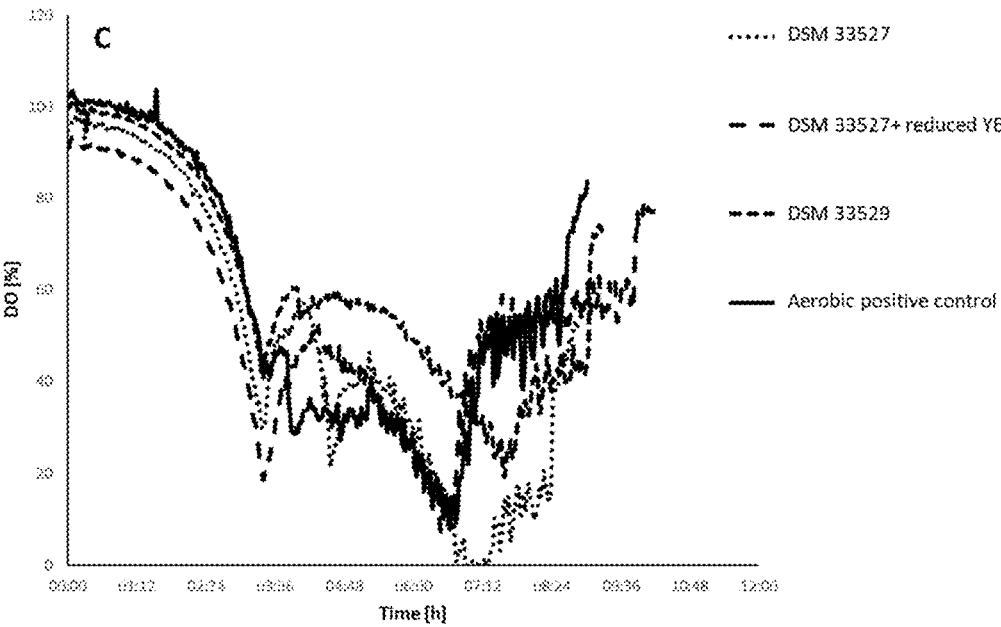
Figure 1D:
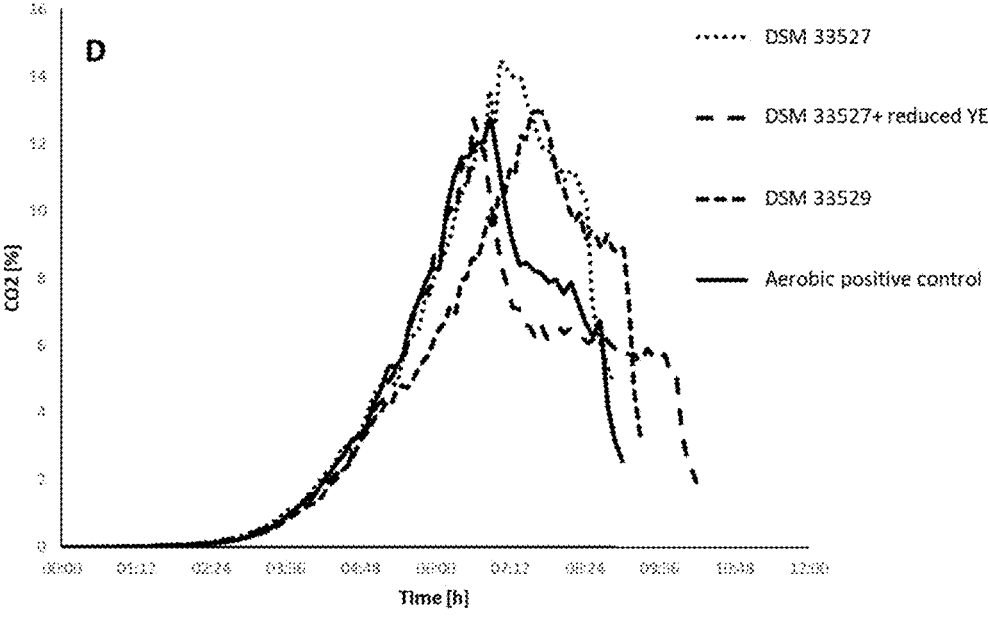

This application is a divisional of U.S. patent application Ser. No. 17/784,055, now U.S. Pat. No. 11,981,890, which is a 35 U.S.C. 371 national application of PCT/EP2020/085582, filed Dec. 10, 2020, which claims priority or the benefit from European Patent Application No. 19214892.2, filed Dec. 10, 2019. The contents of these applications are fully incorporated herein by reference.

TECHNICAL FIELD OF THE INVENTION

The present invention relates to the field of microbial starter cultures. More specifically, the invention provides a method for preparing a microbial starter culture. The microbial starter culture may be a lactic acid bacteria (LAB) starter culture wherein the lactic acid bacteria are inoculated in a culture medium and wherein the culture medium comprises at least one inactivated yeast strain. The novel method applies a vegetarian regulatory-compliant raw material. Therefore, the starter cultures obtained by the new method are useful in the manufacturing of vegetarian food-, feed- and pharmaceutical products.

BACKGROUND OF THE INVENTION

Microbial cultures are used extensively in the food, feed and pharmaceutical industry in the manufacturing of fermented products including most dairy products such as cheese, yoghurt and butter, but also in meat, bakery, wine or vegetable products. Furthermore, microbial cultures are also used to produce proteins including enzymes and various kinds of useful compounds. Such microbial cultures are usually referred to as starter cultures and are produced at industrial propagation plants and distributed to the fermentation industry, such as to a dairy plant, where the starter culture is used in their production processes. In particular cultures of lactic acid bacteria are widely used as starter cultures.

The production of lactic acid bacteria (LAB) starter cultures involves the inoculation of LAB cells in a specific fermentation medium with an appropriate number of the cells to be propagated under appropriate fermentation conditions. In the industrial setting much effort is put into obtaining a high concentration of propagated cells towards the end of the fermentation process. The fermentation conditions and the fermentation medium has to support growth of the cells in order to obtain the desired high biomass yields.

The methods currently applied for the production of starter cultures of lactic acid bacteria, such as *Lactococcus lactis* starter cultures, applies a non-vegetarian compliant source as a raw material in the fermentation media. The non-vegetarian compliant source is applied as an exogenous source. The exogenous source may be a heme source and it is added to support the respiratory process of the lactic acid bacteria. Due to the use of a non-vegetarian compliant heme source such starter cultures obtained by the known methods cannot be applied in vegetarian food-, feed and pharmaceutical products. Therefore, there is a need in the art to develop a respiratory process for the production of microbial starter cultures of e.g. lactic acid bacteria with yields similar to the processes known in the art and wherein the process applies a vegetarian compliant heme source.

SUMMARY OF THE INVENTION

A problem to be solved by the present invention is to provide a microbial culture such as a lactic acid bacterial culture applicable in the manufacturing of vegetarian food-, feed- and pharmaceutical products.

Accordingly, a first aspect the invention relates to a method for obtaining a microbial culture, said method comprises the steps of:
   (i) culturing at least one microbial strain in a culture medium under aeration and obtaining a fermentate,
   (ii) harvesting from the fermentate said at least one microbial strain to obtain the microbial culture,
wherein the culture medium comprises at least one inactivated yeast strain.

In second aspect the invention relates to a culture obtainable by the method of the present invention.

In a third aspect the invention relates to a culture comprising at least one inactivated yeast strain.

A fourth aspect the invention relates to a culture medium comprising at least one inactivated yeast strain.

A fifth aspect of the invention relates to a method of preparing a food product, feed product, a pharmaceutical product, a dairy flavor and a cheese flavoring product, said method comprising adding an effective amount of the culture of the present invention to a food, feed or pharmaceutical product starting material and keeping the inoculated culture under conditions where the at least one microbial strain is metabolically active.

A sixth aspect of the invention relates to a fermented food, feed or pharmaceutical product obtainable by the method of the present invention.

A seventh aspect of the invention relates to the use of at least one inactivated yeast strain in a fermentation method and/or a fermentation process.

DETAILED DISCLOSURE OF THE INVENTION

The inventors have developed a method for obtaining microbial cultures such as starter cultures of microbial strains (e.g. lactic acid bacteria), wherein yeast cells are used as a vegetarian compliant alternative heme source instead of a non-vegetarian compliant heme source. Applying yeast as an exogenous heme source surprisingly showed to support respiration of microbial strains (such as lactic acid bacteria). Yeast is a vegetarian compliant raw material. The novel method provides yields comparable to the methods known in the art.

Prior to discussing the detailed embodiments of the invention a further definition of selected terms used herein is provided.

Herein, the term "purine base" is intended to cover a cyclic nitrogen-containing base having the core structure of purine. Thus, in the present context, the term "purine base" is intended to mean an optionally substituted purine. Specific examples of purine bases include adenine, guanine, xanthine and hypoxanthine.

Analogously, the term "pyrimidine base" is intended to cover a cyclic nitrogen-containing base having the core structure of pyrimidine. Thus, in the present context, the term "pyrimidine base" is intended to mean an optionally substituted pyrimidine. Specific examples of pyrimidine bases include cytosine, thymine and uracil.

In the present context the term "nucleotide" means a 2-deoxyribose (DNA) monomer or a ribose (RNA) monomer which is bonded through its number one carbon atom to a purine base, such as adenine, guanine, xanthine or hypoxanthine, or which is bonded through its number one carbon atom to a pyrimidine base, such as cytosine, thymine or uracil. Further, the DNA or RNA monomer is bonded through its number five-carbon atom to a phosphate group. Specific examples of nucleotides include adenosine monophosphate (AMP), guanosine monophosphate (GMP), uridine monophosphate (UMP), cytidin monophosphate (CMP), xanthine monophosphate (XMP), inosine monophosphate (IMP), deoxyadenosine monophosphate (dAMP), deoxyguanosine monophosphate (dGMP), thymidine monophosphate (dTMP), deoxycytidin monophosphate (dCMP), deoxyxanththin monophosphate (dXMP) and deoxyinosine monophosphate (dIMP). IMP is particularly preferred.

When used herein, the term "nucleoside" is intended to mean a 2-deoxyribose (DNA) monomer or a ribose (RNA) monomer which is bonded through its number one carbon atom to a purine base, such as adenine, guanine, xanthine or hypoxanthine, or which is bonded through its number one carbon atom to a pyrimidine base, such as cytosine, thymine or uracil. Specific examples of nucleosides include adenosine, guanosine, uridine, cytidine, inosine, deoxyadenosine, deoxyguanosine, deoxythymidine, deoxycytidine and deoxyinosine. Inosine is particularly preferred.

As will be understood from the above definitions of the terms "nucleoside" and "nucleotide", a nucleotide may be considered a nucleoside comprising a phosphate group bonded through the number five-carbon atom of the sugar unit. Accordingly, the nucleotides described herein may also be referred to as "nucleoside"-5'-monophosphate. For example, inosinate (IMP) may be referred to as inosine-5'-monophosphate, deoxyinosinate (dIMP) may be referred to as deoxyinosine-5'-monophosphate, etc.

In the present context, the term "derivative", when used in connection with the terms "nucleotide" or "nucleoside" is intended to mean that the nucleotide or the nucleoside in question has been modified in its sugar (i.e. 2-deoxyribose or ribose) unit, or that the nucleotide or the nucleoside in question has been modified in its cyclic nitrogen-containing base, or that the nucleotide or nucleoside in question has been modified in both its sugar unit and in its cyclic nitrogen-containing base. For example, the 2'-H group of the deoxyribose unit or the 2'-OH group of the ribose unit may have been modified, e.g. by incorporation of a 2'-F group, a 2'-O-methyl group, and the like. Likewise, the cyclic nitrogen-containing base may contain one or more substitutents not normally found in adenine, guanine, xanthine, hypoxanthine, cytosine, thymine and uracil. Specific examples include 5-methylcytosine ($^{Me}C$), isocytosine, pseudoisocytosine, 5-bromouracil, 5-propynyluracil, 5-propyny-6-fluorouracil, 5-methylthiazoleuracil, 6-aminopurine, 2-aminopurine, 2,6-diaminopurine, 7-propyne-7-deazaadenine, 7-propyne-7-deazaguanine and 2-chloro-6-aminopurine.

As used herein, the term "fermentation" refers to a process of propagating or cultivating a microbial cell under aerobic or anaerobic conditions.

The term "starter culture" refers to a preparation comprising microbial cells that is intended for inoculating in a medium which is to be fermented.

In the present context, the term "yield" refers to the amount of biomass produced in a fermentation of a given volume. The yield may be measured in various ways; herein the yield is measured in two different ways. 1) As biomass per unit of volume measured (background subtracted) by the Optical Density at 600 nm ($OD_{600}$) of a 1 cm light path of the fermentation medium at the end of the fermentation or 2) by kg of F-DVS culture with an "acidification activity" of 4.8-5.2 according to the according to Pearce test described in Example 3: Analytical Procedure QAm-043 at end of the fermentation.

The term "F-DVS" refers to a so-called frozen Direct Vat Set cultures as described in the Examples.

The term "Porphyrin compound" refers to cyclic tetrapyrrole derivatives whose structures are derived from that of porphyrin by substitution of the carbons located at the apices of the pyrrole core, by various functional groups. It also refers to complexes of the said derivatives with a metal atom that forms coordinate bonds with two of the four nitrogen's of the porphyrin ring. This definition encompasses, but is not limited to: uroporphyrins, coproporphyrins, protoporphyrins and haematoporphyrins, as well as their salts and esters and their complexes with metal atoms. Particularly preferred porphyrin compounds are protoporphyrin IX and its complexes with an iron atom, in particular heme, and the derivatives of chlorophyll, such as chlorophyllins.

The European legal framework on vegetarian claims is currently under revision and at present there are no harmonized rules. All claims under the European food legislation, vegan and vegetarian claims are any message or representation, which is not mandatory under European Union or national legislation, including pictorial, graphic or symbolic representation m in any form, which states, suggests or implies that a food has particular characteristics (Neli Sochirca (2018), EFFL, 6, page 514). Thus, in the present context the term "Vegetarian compliant heme source" refers to a heme source which is not obtained from or derived from an animal and/or multicellular organism. Yeast is a fungus and a single-celled organism. Contrary the term "non-vegetarian compliant heme source" refers to a heme source obtained from or derived from an animal and/or multicellular organism.

In an embodiment of the present invention the one or more microbial strain(s) is/are microbial strains not capable of respiratory growth without supplementation of components/substitute components of the respiratory chain. It will be appreciated that the supplementation of components/substitute components of the respiratory chain may be the supplementation of an exogenous heme source.

The at least one microbial strain may be selected from the group consisting of *Lactococcus, Streptococcus, Lactobacillus* now known as *Lactobacillus, Holzapfelia, Amylolactobacillus, Bombilactobacillus, Companilactobacillus, Lapidilactobacillus, Agrilactobacillus, Schleiferilactobacillus, Loigolactobacilus, Lacticaseibacillus, Latilactobacillus, Dellaglioa, Liquorilactobacillus, Ligilactobacillus, Lactiplantibacillus, Furfurilactobacillus, Paucilactobacillus, Limosilactobacillus, Fructilactobacillus, Acetilactobacillus, Apilactobacillus, Levilactobacillus, Secundilactobacillus* and *Lentilactobacillus* as described in Zheng et al, Int. J. Syst. Evol. Microbiol. DOI 10.1099/ijsem.0.004107, *Leuconostoc, Oenococcus, Weissella, Pediococcus, Enterococcus, Bifidobacterium, Brevibacterium, Propionibacterium* and combinations thereof. The majority of genera in this group are "lactic acid bacteria" however, an industrially important genus is *Bifidobacterium*, although phylogenetically unrelated, is sometimes included in the group of lactic acid bacteria since lactate is one of the main fermentation end products. The list also includes other industrially important starter cultures not included in the lactic acid bacteria genus belong to the genera *Brevibacterium* and *Propionibacterium*.

As used herein the term "lactic acid bacterium" (LAB) designates a gram-positive, microaerophilic or anaerobic bacterium which ferments sugars and produce acids including lactic acid (as the predominantly produced acid) and acetic acid. The industrially most useful lactic acid bacteria are found in the genera *Lactococcus, Streptococcus, Lactobacillus* now known as *Lactobacillus, Holzapfelia, Amylolactobacillus, Bombilactobacillus, Companilactobacillus, Lapidilactobacillus, Agrilactobacillus, Schleiferilactobacillus, Loigolactobacilus, Lacticaseibacillus, Latilactobacillus, Dellaglioa, Liquorilactobacillus, Ligilactobacillus, Lactiplantibacillus, Furfurilactobacillus, Paucilactobacillus, Limosilactobacillus, Fructilactobacillus, Acetilactobacillus, Apilactobacillus, Levilactobacillus, Secundilactobacillus* and *Lentilactobacillus* as described in Zheng et al, Int. J. Syst. Evol. Microbiol. DOI 10.1099/ijsem.0.004107, *Leuconostoc., Oenococcus, Weissella, Pediococcus,* and *Enterococcus*. As mentioned above another industrially important genus is *Bifidobacterium*, although phylogenetically unrelated, it is sometimes included in the group of lactic acid bacteria since lactate is one of the main fermentation end products.

Thus, in one embodiment the at least one lactic acid bacteria is selected from the group consisting of *Lactococcus, Streptococcus, Lactobacillus* now known as *Lactobacillus, Holzapfelia, Amylolactobacillus, Bombilactobacillus, Companilactobacillus, Lapidilactobacillus, Agrilactobacillus, Schleiferilactobacillus, Loigolactobacilus, Lacticaseibacillus, Latilactobacillus, Dellaglioa, Liquorilactobacillus, Ligilactobacillus, Lactiplantibacillus, Furfurilactobacillus, Paucilactobacillus, Limosilactobacillus, Fructilactobacillus, Acetilactobacillus, Apilactobacillus, Levilactobacillus, Secundilactobacillus* and *Lentilactobacillus* as described in Zheng et al, Int. J. Syst. Evol. Microbiol. DOI 10.1099/ijsem.0.004107, *Leuconostoc., Oenococcus, Weissella, Pediococcus, Enterococcus, Bifidobacterium* and combinations thereof.

Commonly used LAB starter culture strains of lactic acid bacteria are generally divided into mesophilic organisms having optimum growth temperatures at about 30° C. and thermophilic organisms having optimum growth temperatures in the range of about 40 to about 45° C.

It will be appreciated that the *Lactobacillus* genus taxonomy was updated in 2020. The new taxonomy is disclosed in Zheng et al. 2020 and the ones important to the present invention are summarized below:

| Current name | New name |
|---|---|
| *Lactobacillus casei* subsp. Casei | *Lacticaseibacillus casei* |
| *Lactobacillus paracasei* subsp. *paracasei* | *Lacticaseibacillus paracasei* subsp. *paracasei* *Lacticaseibacillus paracasei* subsp. *tolerans* |

Typical organisms belonging to the mesophilic group include *Lactococcus lactis, Lactococcus lactis* subsp. *cremoris, Leuconostoc mesenteroides* subsp. *cremoris, Pediococcus pentosaceus, Lactococcus lactis* subsp. *lactis* biovar. *diacetylactis, Lactobacillus casei* subsp. *casei (Lacticaseibacillus casei)* and *Lactobacillus paracasei* subsp. *paracasei (Lacticaseibacillus paracasei* subsp. *paracasei* and *Lacticaseibacillus paracasei* subsp. *tolerans)*. Thermophilic lactic acid bacterial species include as examples *Streptococcus thermophilus, Enterococcus faecium, Lactobacillus delbrueckii* subsp. *lactis, Lactobacillus helveticus, Lactobacillus delbrueckii* subsp. *bulgaricus* and *Lactobacillus acidophilus*.

Due to the fact that the amount and hence the concentration of the yield enhancing agent, the lactic acid bacteria, the inactivated yeast or any other nutrients in the medium may change over time, e.g. due to incorporation into the microbial cells, it is necessary to refer to a specific point in time where the concentration of yield enhancing agent has to be measured or determined. Therefore, the terms "initially" or "before fermentation" (also used herein interchangeably) when used in connection with the concentration of yield enhancing agent, the lactic acid bacteria, the inactivated yeast or any other nutrients in the medium, refers to the concentration of yield enhancing agent, the lactic acid bacteria, the inactivated yeast or any other nutrients present in the medium immediately before the microbial cells to be cultured are added to the medium A significant application of the starter culture according to the invention is as so-called probiotics. In the present context, the term "probiotic" is to be understood as microbial cultures which, when ingested in the form of viable cells by humans or animals, confer an improved health condition, e.g. by suppressing harmful microorganisms in the gastrointestinal tract, by enhancing the immune system or by contributing to the digestion of nutrients. A typical example of such a probiotically active product is "sweet acidophilus milk".

The listing or discussion of an apparently prior-published document in this specification should not necessarily be taken as an acknowledgement that the document is part of the state of the art or is common general knowledge.

Embodiments, preferences and options for a given aspect, feature or parameter of the invention should, unless the context indicates otherwise, be regarded as having been disclosed in combination with any and all embodiments, preferences and options for all other aspects, embodiments, features and parameters of the invention. For example embodiments relevant to the lactic acid bacteria culture obtainable by the method of the present invention may be equally applicable to the lactic acid bacteria starter culture. Also, embodiment stated in relation to the method of the present invention may be relevant to the products of the present invention and vice versa.

Embodiments of the present invention are described below, by way of examples only.

One aspect of the invention relates to a method for obtaining a microbial culture, said method comprises the steps of:

(i) culturing at least one microbial strain in a culture medium under aeration and obtaining a fermentate, (ii) harvesting from the fermentate said at least one microbial strain to obtain the microbial culture, In an embodiment the invention relates to a method for obtaining a lactic acid bacteria culture, said method comprises the steps of:

(i) culturing a lactic acid bacteria in a culture medium under aeration and obtaining a fermentate, (ii) harvesting from the fermentate said lactic acid bacteria to obtain the lactic acid bacteria culture, wherein the culture medium comprises at least one inactivated yeast strain.

In one embodiment the method of the present invention may further comprise a step of:

(iii) concentrating the microbial culture, to obtain a concentrated microbial culture.

In one embodiment the method of the present invention may further comprise a step of:

(iii) concentrating the lactic acid bacterial culture, to obtain concentrated lactic acid bacteria.

The concentrating may be performed using methods known in the art such as but not limited to centrifugation or ultra-filtration. In order to obtain an increased number of microbes (e.g. lactic acid bacteria) in the concentrate obtained in step (iii), it may be contemplated that the concentration factor in step (iv) is in the range from 2 to 20, such as in the range from 6-19, e.g. in the range from 7-18, such as 8-17, e.g. 9-16, such as 10-15, e.g. 11-14, such as 12-13, e.g. 2-4, such as 3-6.

Commercial starter cultures may commonly be distributed as frozen cultures. At the low temperatures at which such frozen cultures typically are maintained most metabolic activities in the cell ceases and cells can be maintained in this suspended, but viable, state for extended periods.

Concentrated frozen cultures are commercially very interesting since such cultures can be inoculated directly into the production container. By using such concentrated frozen cultures, the end-user avoids the otherwise obligatory, time-consuming intermediary fermentation step during which the starter culture are amplified, and the end-user furthermore reduces the risk of contamination drastically. Such concentrated cultures may be referred to as DVS—direct vat Set™ cultures.

As an alternative to the concentrated frozen cultures concentrated freeze dried direct vat Set™ cultures, FD-DVS™, may be prepared. Such cultures have the additional advantage that they can be shipped without refrigeration.

Thus, in an embodiment the method of the present invention may further comprise a step of:

(iv) freezing said microbial bacterial culture of step (ii) or the concentrated microbial culture in step (iii) to obtain a frozen microbial culture.

Thus, in an embodiment the method of the present invention may further comprise a step of:

(iv) freezing said lactic acid bacterial culture of step (ii) or the concentrated lactic acid bacteria in step (iii) to obtain a frozen lactic acid bacterial culture.

In order to remove liquid from the frozen microbial bacterial culture, the method of the present invention may further comprise a step of:

(v) sublimating water from said frozen microbial culture to obtain a dried microbial culture.

In order to remove liquid from the frozen lactic acid bacterial culture, the method of the present invention may further comprise a step of:

(v) sublimating water from said frozen lactic acid bacterial culture to obtain a dried lactic acid bacterial culture.

Step (v) may be carried out by a technique selected form the group consisting of spray drying, spray freezing, vacuum drying, air drying, freeze drying, tray trying and vacuum tray drying. In a further embodiment the method of the present invention further comprises a step of:

(vii) packing said frozen microbial culture obtained in step (iv) or the freeze-dried microbial culture obtained in step (v).

It may be appreciated that the method of the present invention further comprises a step of:

(vii) packing said frozen lactic acid bacterial culture obtained in step (iv) or the dried lactic acid bacterial culture obtained in step (v).

Often damaging effects of freezing and thawing on the viability of living cells has been observed. In general they are ascribed to cell dehydration and the formation of ice crystals in the cytosol during freezing.

However, a number of cryoprotective agents have been found to ensure that freezing occur in a controlled and minimally injurious manner, e.g. by ensuring that ice crystallization in the cytosol is precluded or minimized during freezing.

Preferably, at least one cryoprotectant is added to the harvested microbial culture or to the harvested lactic acid bacteria culture obtained in step (ii) or to the concentrated microbial culture or the concentrated lactic acid bacterial culture obtained in step (iii)

Preferably, the cryoprotective agent(s) is selected from the group consisting one or more compound(s) involved in the biosynthesis of nucleic acids or one or more derivative(s) of any such compounds. Examples of preferred cryoprotective agent(s) suitable to be added to the harvested microorganism corresponds essentially to the preferred yield enhancing agent(s) as described herein. Addition of such cryoprotective agent(s) to harvested microorganism is described in an earlier filed patent application with application number PCT/DK2004/000477. Preferred cryoprotective agent(s) described in PCT/DK2004/000477 are also preferred cryoprotective agent(s) of the present invention. The complete description of PCT/DK2004/000477 is incorporated by reference herein. In a further preferred embodiment of the invention the one or more cryoprotective agent(s) is/are selected from the group of nucleoside monophosphates. In a preferred embodiment at least one or the only cryoprotective agent is IMP. Carbohydrate or proteinaous type cryoprotectant agents are not in general described to increase the metabolic activity of thawed or reconstituted cultures. The cryoprotective agents of the invention may in addition to their cryoprotective activity also confers an increased metabolic activity (booster effect) of the culture when it is inoculated into the medium to be fermented, processed or converted. Thus one embodiment of the invention is a frozen or dried culture, wherein the cryoprotective agent is an agent or mixture of agents, which in addition to its cryoprotectivity has a booster effect. The expression "booster effect" is used to describe the situation wherein the cryoprotective agent confers an increased metabolic activity (booster effect) on to the thawed or reconstituted culture when it is inoculated into the medium to be fermented or converted. Viability and metabolic activity are not synonymous concepts. Commercial frozen or dried (e.g. freeze dried) cultures may retain their viability, although they may have lost a significant portion of their metabolic activity e.g. cultures may lose their acid-producing (acidification) activity when kept stored even for shorter periods of time. Thus viability and booster effect has to be evaluated by different assays. Whereas viability is assessed by viability assays such as the determination of colony forming units, booster effect is assessed by quantifying the relevant metabolic activity of the thawed or reconstituted culture relative to the viability of the culture. The acidifying activity assay described below is one example of an assay quantifying the relevant metabolic activity of the thawed or reconstituted culture.

Although the acid-producing activity is exemplified herein, this invention is intended to encompass the stabilization of any types of metabolic activities of a culture. Thus, the term "metabolic activity" refers to the oxygen removal activity of the cultures, its acid-producing activity, i.e. the production of e.g. lactic acid, acetic acid, formic acid and/or propionic acid, or its metabolite producing activity such as the production of aroma compounds such as acetaldehyde, (a-acetolactate, acetoin, diacetyl and 2,3-butylene glycol (butanediol)).

In an embodiment of the invention the frozen culture contains or comprises from 0.2% to 20% of the cryoprotective agent or mixture of agents measured as % w/w of the frozen material. It is, however, preferable to add the cryo-protective agent or mixture of agents at an amount which is in the range from 0.2% to 15%, more preferably within the range of 0.2% to 10%, more preferably within the range of 0.5% to 7%, and more preferably within the range of 1% to 6% by weight, including within the range of 2% to 5% of the cryoprotective agent or mixture of agents measured as % w/w of the frozen material by weight. In a preferred embodi-ment the culture comprises approximately 3% of the cryo-protective agent or mixture of agents measured as % w/w of the frozen material by weight. The preferred amount of approximately 3% of the cryoprotective agent corresponds to concentrations in the 100 mM range. It should be recog-nized that for each aspect of embodiment of the invention the ranges may be increments of the described ranges.

In the case that the culture is a dried culture (e.g. freeze dried) it is preferred to add the cryoprotective agent or mixture of agents at an amount, which is in the range of 0.8% to 60% by weight, or within the range of 0.8% to 55% by weight, or within the range of 1.3% to 40% by weight, or within the range of 3% to 30% by weight, or within the range of 6% to 25% by weight, including the range of 10% to 24% by weight of the dried culture. In a preferred embodiment the dried culture (e.g. freeze dried) comprises approximately 16% of the cryoprotective agent or mixture of agents mea-sured as % w/w of the dried culture.

Additionally, the frozen or dried culture may contain further conventional additives including nutrients such as yeast extract, sugars, antioxidants, inert gases and vitamins etc. Also surfactants including Tween® compounds can be used as further additive to the culture according to the invention. Further examples of such conventional additives, which in addition may be added to the culture according to the invention, may be selected from proteins, protein hydro-lysates and amino acids. Preferred suitable examples of these include the ones selected from the group consisting of Glutamic acid, Lysine, Na-glutamate, Na-caseinate, Malt extract, Skimmed milk powder, Whey powder, Yeast extract, Gluten, Collagen, Gelatin, Elastin, Keratin, and Albumins or mixtures thereto.

More preferably the conventional additives is a carbohy-drate. Suitable examples of these include the ones selected from the group consisting of Pentoses (eg. Ribose, Xylose), Hexoses (e.g. fructose, mannose, Sorbose), Disaccharides (eg. Sucrose, Trehalose, Melibiose, Lactulose), Oligo sac-charides (e.g. Raffinose), Oligofrutoses (eg. Actilight, Fri-broloses), Polysaccharides (e.g. Maltodextrins, Xanthan Gum, Pectin, Alginate, Microcrystalline cellulose, Dextran, PEG), and Sugar alcohols (Sorbitol, Manitol and Inositol).

It is presently preferred that the ratio (wt %/wt %) of the at least one cryoprotectant to the concentrated microbial culture or the concentrated lactic acid bacteria culture is within the range from 1:0.5 to 1:5, such as from 1:1 to 1:4 or from 1:1½ to 1:3.

An alternative embodiment of the invention is the method of preparing a microbial culture in increased yields as described herein and which further comprise that the con-centrated microbial culture or the concentrated lactic acid bacterial culture obtained in step (iii) is dried by freeze drying, tray trying, spray drying, spray freezing, vacuum drying, air drying or any drying process which is suitable for drying of bacterial cultures.

The at least one inactivated yeast strain may be present in the culture medium or added to the culture medium before the at least one microbial strain and/or the lactic acid bacteria is/are added to the medium or alternatively, the at least one inactivated yeast strain may be added immediately after the at least one microbial strain and/or the lactic acid bacteria have been added to the culture medium. In one embodiment the at least one inactivated yeast strain is a heat inactivated yeast strain. The heat inactivation may be per-formed by any method known in the art, such as but not limited to autoclavation and/or UHT.

In a preferred embodiment the at least one inactivated yeast strain is a whole cell yeast. One of the differences between the method of the present invention and the meth-ods of the prior art is that the at least one inactivated yeast strain may be a whole cell yeast. A whole yeast cell differs from e.g. yeast extract in that the cell wall of a whole yeast cell is intact. A yeast extract is made from lysed yeast cells and thus, a yeast extract comprises only fragments of the yeast cell wall not intact yeast cell walls. An intact yeast cell can be determined under a microscope. If the cell wall is lysed no cell walls can be seen in the microscope whereas a cell with an intact cell wall can be seen under the microscope as an intact whole cell.

The at least one inactivated yeast strain is added to or present in the culture medium as a raw material intended to aid fermentation. The present inventors surprisingly discov-ered that the application of a non-vegetarian source in the culture medium may be replaced with at least one inacti-vated yeast strain without a decrease in yield. One way of determining whether the at least one yeast strain is an inactivated yeast strain is by spread the inactivated yeast on YGC agar plates and incubated at 4 days at 25° C.—if no growth occurs the yeast is an inactivated yeast. It may therefore be contemplated that the inactivated yeast is a yeast non-culturable when spread on YGC agar plates and incubated at 4 days at 25° C. An aspect of the present invention therefore relates to the use of at least one inacti-vated yeast strain in a fermentation method and/or fermen-tation process.

The culture medium in step (i) may be a complex fer-mentation medium.

The complex fermentation medium may be any complex fermentation medium known in the art however the complex fermentation medium may comprise compounds selected from the group consisting of lactose, nutrients, vitamins tryptone, soya peptone, yeast extract, Ascorbic acid, Mag-nesium sulphate and combinations thereof.

It may be contemplated that at least one porphyrin com-pound is present in or is added to the culture medium. Likewise, it may be contemplated that at least one yield enhancing agent is present in or is added to the culture medium.

It may be contemplated that the yield of the novel method relates to a situation wherein at least one yield enhancing agent continues to appear in the fermentation medium throughout the complete fermentation. It has been observed that the exhausting of yield enhancing agents from the medium result in the onset of de novo synthesis of various enzyme systems and it is assumed that such energy-demand-ing de novo synthesis results in a reduced yield.

The situation wherein at least one yield enhancing agent continues to appear in the fermentation medium throughout the complete fermentation may be obtained by culturing the at least on microbial strain such as the LAB in a medium which initially comprise sufficient yield enhancing agent to ensure that at least one such agent remain in the medium throughout the complete fermentation. One such medium is a culture medium (i.e. before the at least one microbial strain(s) is/are added). comprising in the range of at least 3 m M to at least 5 m M, e.g. in the range from 3 m M-4 m M, e.g at least 3 m M, such as 4 m M or e.g. 5 m M of at least one yield enhancing agent selected from the group consisting one or more compound(s) involved in the bio-synthesis of nucleic acids or one or more derivative(s) of any such compounds.

Such medium may be obtained by formulating the media using components which are particularly rich with respect to yield enhancing agents selected from the group consisting one or more compound(s) involved in the biosynthesis of nucleic acids or one or more derivative(s) of any such compounds.

Instead of formulating the medium using preparations, which are particularly rich in yield enhancing agents, puri-fied agents may be added to otherwise standard media formulations. For instance the culture medium may be a complex fermentation medium to which at least 0.2 g, preferably at least 0.8 g and even more preferred at least 2 g of at least one yield enhancing agent has been added per L complex fermentation medium (i.e. before the at least one microbial strain(s) is/are added).

It is also possible to ensure that at least one yield enhancing agent remain in the medium throughout the complete fermentation by one or more additions of said at least one yield enhancing agent is added the fermentation.

In a preferred embodiment said yield enhancing agent is selected from the group consisting of a purine base, a pyrimidine base, a nucleoside, a nucleotide and derivatives thereof.

In an embodiment of the present invention the yield enhancing agent is a purine base Said yield enhancing agent may be a purine base prefer-ably a purine base is selected from the group consisting of adenine, guanine, xanthine and hypoxanthine.

In a further embodiment the yield enhancing agent is a pyrimidine base

Said yield enhancing agent may be a pyrimidine base, preferably a pyrimidine base is selected from the group consisting of cytosine, thymine and uracil.

In yet an embodiment the yield enhancing agent is a nucleoside.

Said yield enhancing agent may be a nucleoside, prefer-ably, wherein said nucleoside is selected from the group consisting of adenosine, guanosine, uridine, cytidine, inos-ine, deoxyadenosine, deoxyguanosine, deoxythymidine, deoxycytidine and deoxyinosine.

In a preferred embodiment said nucleoside is selected from the group consisting of adenosine, guanosine, uridine, cytidine, thymidine and inosine. Most preferably, wherein said nucleoside is inosine.

In a further embodiment the yield enhancing agent is a nucleotide.

Said yield enhancing agent may be a nucleotide, prefer-ably wherein said nucleotide is selected from the group consisting of adenosine monophosphate (AMP), guanosine monophosphate (GMP), uridine monophosphate (UMP), cytidin monophosphate (CMP), xanthine monophosphate (XMP), inosine monophosphate (IMP), deoxyadenosine monophosphate (dAMP), deoxyguanosine monophosphate (dGMP), thymidine monophosphate (dTMP), deoxycytidin monophosphate (dCMP), deoxyxanththin monophosphate (dXMP) and deoxyinosine monophosphate (dIMP).

In a preferred embodiment said nucleotide is selected from the group consisting of AMP, GMP, UMP, CMP, XMP and IMP. Most preferably, wherein said nucleotide is IMP.

A preferred embodiment is wherein said culture medium comprises at least two yield enhancing agents preferably selected from the group consisting of a purine base, a pyrimidine base, a nucleoside, a nucleotide and derivatives thereof.

Preferably said culture medium comprises at least two yield enhancing agents selected from the group consisting of a nucleoside and a nucleotide. Most preferably wherein said nucleoside is inosine and said nucleotide is IMP.

A preferred embodiment is wherein said culture medium initially comprises (i.e. before the at least one microbial strain(s) is/are added) or the culture medium in step (i) comprises from 1 to 70 mM of each yield enhancing agent.

More preferably, wherein said culture medium initially comprises (i.e. before the at least one microbial strain(s) is/are added) or the culture medium in step (i) comprises from 1 to 60 mM of each yield enhancing agent, such as from 1.3 to 60 mM, e.g. from 1.5 to 50 mM, preferably from 2 to 40 mM, such as from 2.5 to 30 mM, e.g. from 3 to 20 mM, more preferably from 3 to 15 mM, such as from 4 to 10 mM, e.g. about 7 mM.

In one embodiment the culture medium in step (i) com-prises at least 0.5% w/w of the at least one inactivated yeast strain before fermentation (i.e. before the at least one micro-bial strain(s) is/are added), such as 1% w/w, e.g. 2% w/w, such as 3% w/w, e.g. 4% w/w, such as in the range from 0.5-4% w/w, e.g. 1-3.5% w/w, such as 1.5-3% w/w, e.g. 2-2.5% w/w of the at least one inactivated yeast stain to the weight of the culture medium (i.e. before the at least one microbial strain(s) is/are added)

In a further embodiment the culture medium in step (i) comprises at least 0.5% w/w of the microbial inoculation culture such as an lactic acid bacteria inoculation culture before fermentation, such as at least 1% w/w, e.g. 1.5% w/w, such as 2% w/w, e.g. 2.5% w/w, such as 3% w/w, e.g. 3.5% w/w, such as 4% w/w, such as in the range from 0.5-4% w/w, e.g. 1-3.5% w/w, such as 1.5-3% w/w, e.g. 2-2.5% w/w of the at lactic acid bacteria inoculation culture before fermen-tation to the weight of the culture medium (i.e. before the at least one microbial strain(s) is/are added). The inoculation culture may be made according to the method specified in Example 1.

Surprisingly, by the method of the present invention it is occasionally possible to obtain a microbial culture such as lactic acid bacteria cultures that are sufficiently concentrated to be used for production of F-DVS without concentration of the culture. However even when the present method applied most cultures need to be concentrated to obtain starter cultures of commercial interest. Such cultures may prefer-ably be harvested and concentrated by centrifugation or ultra-filtration.

It may be contemplated that the lactic acid bacteria is cultured under high Optical Density-conditions. In the pres-ent context the culturing under high Optical Density-condi-tions is to be understood as culturing at least one microbial strain(s) such as a lactic acid bacteria in a culture medium at conditions that allows the fermentation to proceed beyond an Optical Density measured at 600 nm ($OD_{600}$) of 10. In a preferred embodiment the culturing of the microorganism is done at industrial relevant conditions under high Optical Density-conditions.

In a selected embodiment of the present invention said high Optical Density-conditions are characterized by an $OD_{600}$ above 15, preferably above 20, more preferably above 30, even more preferably over 40 and most preferably over 50 at the termination of the fermentation or in step (ii).

Thus, in one embodiment high Optical Density conditions are characterized by an $OD_{600}$ above 10 in the culture medium of step (ii). Thus, $OD_{600}$ of the culture medium in step (ii) may be in the range from $OD_{600}$=10 to $OD_{600}$=200, more preferably a OD of from $OD_{600}$=15 to $OD_{600}$=100 and most preferably a OD of from $OD_{600}$=20 to $OD_{600}$=80.

Accordingly, a preferred embodiment is wherein the Optical Density (OD) of the culture at 600 nm of 1 cm light path medium reached a OD of from $OD_{600}$=10 to $OD_{600}$=200, more preferably a OD of from $OD_{600}$=15 to $OD_{600}$=100, even more preferred a OD of from a OD of from $OD_{600}$=20 to $OD_{600}$=90 and most preferably a OD of from $OD_{600}$=25 to $OD_{600}$=80.

Further, a preferred embodiment is wherein the culturing is performed in a large-scale fermentor comprising of from 5 L to 100.000 L culture medium, preferably of from 300 L to 20.000 L culture medium.

A preferred embodiment is wherein the culturing comprising control of temperature and/or pH.

In an embodiment the culture medium in step (i) and/or step (ii) comprises one or more microbial strain(s) is/are microbial strains that are not capable of respiratory growth without supplementation of components/substitute components of the respiratory chain.

In an embodiment the culture medium in step (i) and/or step (ii) comprises at least one microbial strain selected from the group consisting of *Lactococcus, Streptococcus, Lactobacillus* now known as *Lactobacillus, Holzapfelia, Amylolactobacillus, Bombilactobacillus, Companilactobacillus, Lapidilactobacillus, Agrilactobacillus, Schleiferilactobacillus, Loigolactobacilus, Lacticaseibacillus, Latilactobacillus, Dellaglioa, Liquorilactobacillus, Ligilactobacillus, Lactiplantibacillus, Furfurilactobacillus, Paucilactobacillus, Limosilactobacillus, Fructilactobacillus, Acetilactobacillus, Apilactobacillus, Levilactobacillus, Secundilactobacillus* and *Lentilactobacillus* as described in Zheng et al, Int. J. Syst. Evol. Microbiol. DOI 10.1099/ijsem.0.004107, *Leuconostoc., Oenococcus, Weissella, Pediococcus, Enterococcus, Bifidobacterium, Brevibacterium, Propionibacterium* and combinations thereof.

In an embodiment the culture medium in step (i) and/or step (ii) comprises at least one lactic acid bacteria selected from the group consisting of *Lactococcus, Streptococcus, Lactobacillus* now known as *Lactobacillus, Holzapfelia, Amylolactobacillus, Bombilactobacillus, Companilactobacillus, Lapidilactobacillus, Agrilactobacillus, Schleiferilactobacillus, Loigolactobacilus, Lacticaseibacillus, Latilactobacillus, Dellaglioa, Liquorilactobacillus, Ligilactobacillus, Lactiplantibacillus, Furfurilactobacillus, Paucilactobacillus, Limosilactobacillus, Fructilactobacillus, Acetilactobacillus, Apilactobacillus, Levilactobacillus, Secundilactobacillus* and *Lentilactobacillus* as described in Zheng et al, Int. J. Syst. Evol. Microbiol. DOI 10.1099/ijsem.0.004107, *Leuconostoc., Oenococcus, Weissella, Pediococcus, Enterococcus.* and *Bifidobacterium.*

In an embodiment the culture medium in step (i) and/or step (ii) comprises one or more mesophilic organisms selected from the group comprising *Lactococcus lactis, Lactococcus lactis* subsp. *cremoris, Leuconostoc mesenteroides* subsp. *cremoris, Pediococcus pentosaceus, Lactococcus lactis* subsp. *lactis* biovar. *diacetylactis, Lactobacillus casei* subsp. *casei* (new name *Lacticaseibacillus casei*), *Lactobacillus paracasei* subsp. *Paracasei* ((*Lacticaseibacillus paracasei* subsp. *paracasei* and *Lacticaseibacillus paracasei* subsp. *tolerans*).) and *Oenococcus oeni.*

In a further embodiment the culture medium in step (i) and/or step (ii) comprises one or more thermophilic organisms having optimum growth temperatures at about 40° C. to about 45° C.

In yet and embodiment the culture medium in step (i) and/or step (ii) comprises one or more thermophilic organisms selected from the group comprising *Streptococcus thermophilus, Enterococcus faecium, Lactobacillus delbrueckii* subsp. *lactis, Lactobacillus helveticus, Lactobacillus delbrueckii* subsp. *bulgaricus* and *Lactobacillus acidophilus.*

In an embodiment, the culture medium in step (i) and/or step (ii) is a LD-culture that comprises one or more organisms selected from the group comprising *Lactococcus lactis* subsp. *lactis, Lactococcus lactis* subsp. *cremoris, Lactococcus lactis* subsp. *lactis* biovar. *diacetylactis* and *Leuconostoc mesenteroides* subsp. *cremoris.* In the present context the term "LD-culture" is to be understood as the combination of the species *Lactococcus lactis* and the species *Leuconostoc.*

It may be appreciated that the culture medium in step (i) and/or step (ii) is an O-culture that comprises one or more organisms selected from the group comprising *Lactococcus lactis* subsp. *lactis* and *Lactococcus lactis* subsp. *cremoris.* In the present context "O-culture" is to be understood as a culture medium comprising *Lactococcus lactis* subsp. *lactis* and *Lactococcus lactis* subsp. *cremoris.* O-cultures are typically used to make cheese without holes (Cheddar, Cheshire, Feta). The particular culture is commercially available under the name R 604 from Chr. Hansen A/S, Denmark (catalogue no. 200113).

In a preferred embodiment culture medium in step (i) and/or step (ii) is a culture comprising *Lactococcus lactis.*

In an embodiment the at least one yeast strain is selected from the group consisting of *Torulaspora delbrueckii, Saccharomyces cerevisiae, Pichia kluyveri, Debaromyces hansenii, Lachancea thermotolerans, Torula* Yeast and combinations thereof.

In a preferred embodiment the at least one yeast strain is selected from the group consisting of *Torulaspora delbrueckii, Saccharomyces cerevisiae* and combinations thereof.

Particular preferred yeast strains for use in the invention are selected from the group consisting of *Torulaspora delbrueckii* deposited as DSM 33529 on 27 May 2020 by Chr. Hansen A/S, Denmark), *Saccharomyces cerevisiae* deposited as DSM 33527 on 27 May 2020 by Chr. Hansen A/S, Denmark) and

*Saccharomyces cerevisiae* deposited as DSM 33528 on 27 May 2020 by Chr. Hansen A/S, Denmark) which all have been deposited at the depository DSMZ of Inhoffenstrasse 25 7B, 38124 Braunschweig, Germany under the Expert Solution option and in accordance with the provisions of the Budapest Treaty.

A preferred embodiment of the invention relates to a method for obtaining a microbial culture, said method comprises the steps of:

(i) culturing at least one microbial strain(s) in a culture medium under aeration and obtaining a fermentate, (ii) harvesting from the fermentate said at least one microbial strain(s) to obtain the microbial culture, wherein the culture medium comprises at least one inactivated yeast strain and wherein the at least one inactivated yeast strain is selected from the group consisting of *Torulaspora delbrueckii* deposited as DSM 33529, *Saccharomyces cerevisiae* deposited as DSM 33527, *Saccharomyces cerevisiae* deposited as DSM 33528 and combinations thereof.

A preferred embodiment of the invention relates to a method for obtaining a microbial culture, said method comprises the steps of:

(i) culturing at least one microbial strain(s) in a culture medium under aeration and obtaining a fermentate, (ii) harvesting from the fermentate said at least one microbial strain(s) to obtain the microbial culture, wherein the culture medium comprises at least one heat inactivated yeast strain and wherein the at least one inactivated yeast strain is selected from the group consisting of *Torulaspora delbrueckii* deposited as DSM 33529, *Saccharomyces cerevisiae* deposited as DSM 33527, *Saccharomyces cerevisiae* deposited as DSM 33528 and combinations thereof.

A preferred embodiment of the invention relates to a method for obtaining a lactic acid bacteria culture, said method comprises the steps of:

(i) culturing a lactic acid bacteria in a culture medium under aeration and obtaining a fermentate, (ii) harvesting from the fermentate said lactic acid bacteria to obtain the lactic acid bacteria culture, wherein the culture medium comprises at least one inactivated yeast strain and wherein the at least one inactivated yeast strain is selected from the group consisting of *Torulaspora delbrueckii* deposited as DSM 33529, *Saccharomyces cerevisiae* deposited as DSM 33527, *Saccharomyces cerevisiae* deposited as DSM 33528 and combinations thereof.

In a further preferred embodiment the invention relates to a method for obtaining a lactic acid bacteria culture, said method comprises the steps of:

(i) culturing a lactic acid bacteria in a culture medium under aeration and obtaining a fermentate, (ii) harvesting from the fermentate said lactic acid bacteria to obtain the lactic acid bacteria culture, wherein the culture medium comprises at least one heat inactivated yeast strain and wherein the at least one inactivated yeast strain is selected from the group consisting of *Torulaspora delbrueckii* deposited as DSM 33529, *Saccharomyces cerevisiae* deposited as DSM 33527, *Saccharomyces cerevisiae* deposited as DSM 33528 and combinations thereof.

The culture may be aerated so as to maintain, during the whole duration of the culture, an oxygen content which is equal to at least 5 millimoles per litre of culture medium.

In order to obtain maximum yield, it may be preferred that the harvest in step (ii) is performed 5 and 24 hours after the start of the culture The method of the present invention may further comprise storage of the harvested microbial culture or the lactic acid bacteria culture obtained in step (ii) or the concentrated microbial culture or the lactic acid bacteria culture obtained in step (iii)

Due to the high yield of the novel method the microbial culture in the fermentate obtained in step (i) may comprises in the range of 2.0E+10-5.0E+10 active microbial cells/g microbial culture, such as 2.5E+10-4.5E+10, e.g. 3.0E+10-4.0E+10 active microbial cells cells/g microbial culture. Likewise, the microbial culture in the fermentate obtained in step (i) may comprise in the range of 2.0E+10-5.0E+10 total microbial cells/g microbial culture, such as 2.5E+10-4.5E+10, e.g. 3.0E+10-4.0E+10 total 1 microbial cells/g microbial culture. In table 2 in the experimental part it can be seen that the number of active lactic acid bacterial cells and the total number of lactic acid bacterial cells are almost identical thus, indicating that the lactic acid bacterial culture and the lactic acid bacterial starter culture obtainable by the present invention has high viability.

Due to the high yield of the novel method the lactic acid bacterial culture in the fermentate obtained in step (i) may comprises in the range of 2.0E+10-5.0E+10 active lactic acid bacterial cells/g lactic acid bacterial culture, such as 2.5E+10-4.5E+10, e.g. 3.0E+10-4.0E+10 active lactic acid bacterial cells/g lactic acid bacterial culture. Likewise, the lactic acid bacterial culture in the fermentate obtained in step (i) may comprise in the range of 2.0E+10-5.0E+10 total lactic acid bacterial cells/g acid bacterial culture, such as 2.5E+10-4.5E+10, e.g. 3.0E+10-4.0E+10 total lactic acid bacterial cells/g acid bacterial culture. In table 2 in the experimental part it can be seen that the number of active lactic acid bacterial cells and the total number of lactic acid bacterial cells are almost identical thus, indicating that the lactic acid bacterial culture and the lactic acid bacterial starter culture obtainable by the present invention has high viability.

The number of active and/or total cells are determined using flowcytometry which is technique known to the skilled person.

In a preferred embodiment, wherein said increased yield of the harvested microbial strain(s) e.g. lactic acid bacteria or the microbial culture such as a lactic acid bacterial culture of the method is increased by a factor of at least 1.2, preferably by a factor of at least 1.3, more preferably by a factor of at least 1.4, even more preferably by a factor of at least 1.5 and most preferably by a factor of at least 1.6 compared to the Anaerobic process excluding heme source process.

The Anaerobic process excluding heme source is disclosed in Example 1 whereas the Aerobic respiratory process including non-vegetarian heme source is disclosed in Example 3.

According to the invention the microorganisms are fermented at aerobic conditions. Preferably the fermentation of the lactic acid bacteria is performed under aeration and in a culture medium, in which at least one porphyrin compound is present or is added. In a preferred embodiment the LAB is cultured under aeration in a prophyrin-containing culture medium wherein said medium further comprise at least one yield enhancing agent selected from the group consisting one or more compound(s) involved in the biosynthesis of nucleic acids or one or more derivative(s) of any such compounds. Aeration can be effected by any means known by one skilled in the Art, for example by shaking or stirring the culture medium, or by passing a gaseous mixture containing oxygen such as air, into the culture medium.

In a second aspect the invention relates to a microbial culture such as a starter culture obtainable by the method of the present invention. The microbial culture such as the starter culture may be provided as a culture concentrate such as a starter culture concentrate.

In third aspect the invention relates to a microbial culture such as a starter culture comprising at least one inactivated yeast strain.

A fourth aspect relates to a culture medium comprising at least one inactivated yeast strain.

In a fifth aspect the invention relates to a method of preparing a food product, feed product, a pharmaceutical product, a dairy flavor.

cheese flavoring product, said method comprising adding an effective amount of the culture of the present invention to a food, feed or pharmaceutical product starting material and keeping the inoculated culture under conditions where the at least one microbial strain is metabolically active Preferably the food product of the fifth aspect of the invention is selected from the group consisting of a milk-based product, a vegetable product, a meat product, a beverage, a fruit juice, a wine, a bakery product, a dairy flavor and a cheese flavoring product.

Preferably the milk-based product is selected from the group consisting of a cheese, yoghurt, a butter, an inoculated sweet milk and a liquid fermented milk product.

In a sixth aspect the invention relates to a fermented food, feed or pharmaceutical product obtainable by the method of the present invention.

A seventh aspect of the invention relates to the use of at least one inactivated yeast strain in a fermentation method and/or a fermentation process.

In an interesting aspect, the present invention provides a method for obtaining increased yield(s) of microbially produced compound(s), said method comprising the steps of
   i) culturing at least one microbial strain(s) in a culture medium comprising at least on inactivated yeast strain; and
   ii) obtaining said microbially produced compound(s),
wherein the method provides an increased yield of microbially produced compound(s) as compared to culturing the at least one microbial strain(s) in an identical medium without the at least one inactivated yeast strain.

In an interesting aspect, the present invention provides a method for obtaining increased yield(s) of microbially produced compound(s), said method comprising the steps of
   i) culturing a lactic acid bacteria in a culture medium comprising at least on inactivated yeast strain; and
   iii) obtaining said microbially produced compound(s),
wherein the method provides an increased yield of microbially produced compound(s) as compared to culturing the microorganism in an identical medium without the at least one inactivated yeast strain.

Compounds produced by microbial organisms as described includes but are not limited to enzymes, proteins, metabolites, glycolipids, antibiotics, bacteriocins, amino acids, flavors, volatiles. Such compounds may be produced by recombinant DNA technology or by conventional means.

The invention is further illustrated in the following non-limiting examples and the figures wherein.

FIGURE LEGENDS

FIGS. 1A-1D. Trend curves of A) Base flow (FIG. 1A), B) Total base used (FIG. 1B), C) Dissolved oxygen (DO %) (FIG. 1C) and D) CO2 (FIG. 1D) for *Lactococcus lactis* during fermentation. The curves are shown respiratory growth with the yeasts that support respiration, *Torulaspora delbrueckii* (DSM 33529), *Saccharomyces cerevisiae* (DSM 33527) and *Saccharomyces cerevisiae* (DSM 33527) with yeast extract reduction by 40% in production media. Controls are Aerobic positive control, which is a respiratory fermentation process with a non-vegetarian compliant heme source and an Anaerobic negative control, which is an anaerobic (and vegetarian) fermentation run with N2 in headspace and therefore without DO probe and off-gas analysis. There are no curves of the Anaerobic negative control in graphs C and D since DO % and CO2 are not measured for this process.

Figure 2:
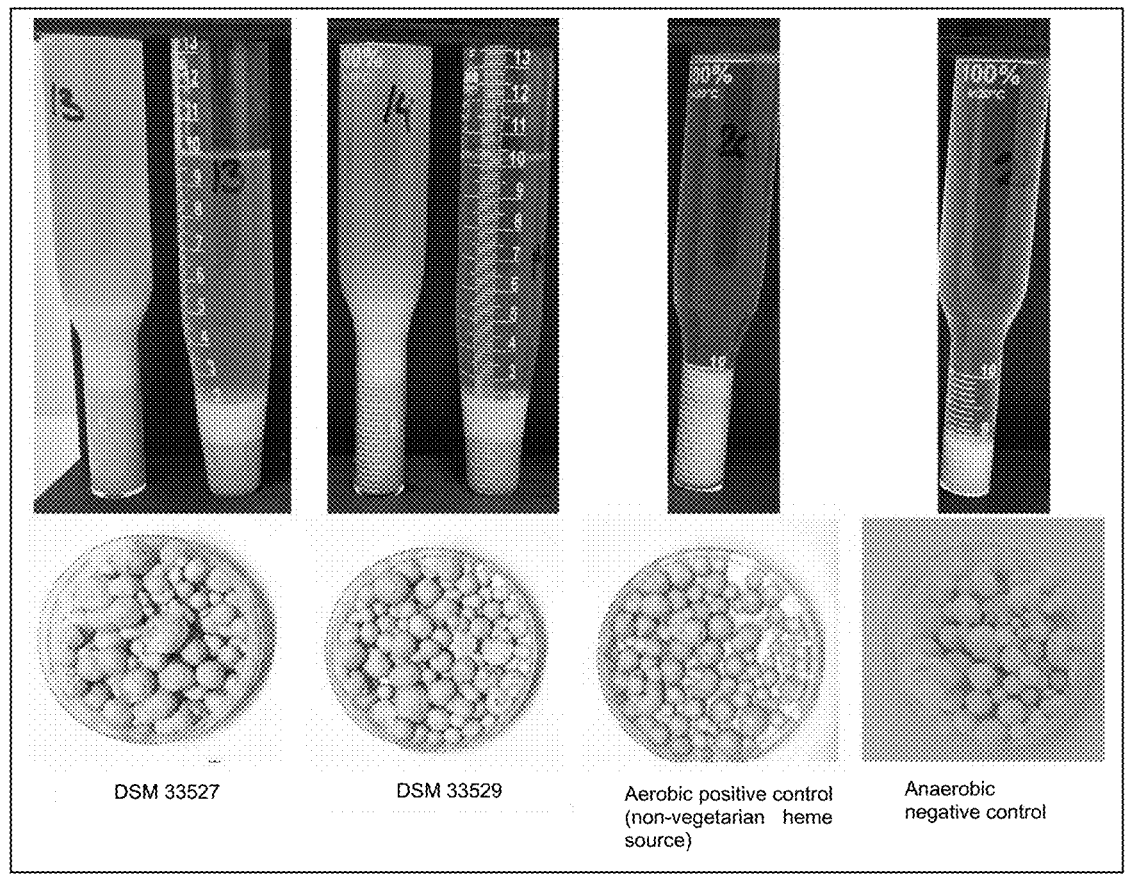

FIG. 2. Packed cell volume of end of fermentation and Appearance of the final product (F-DVS). From left to right: Yeast cells as heme source (DSM 33527 and DSM 33529 as representative), small and large PCV tube; Aerobic positive control; Anaerobic negative control. Large PCV tubes helps to have more precise indication of the amounts of cells and yeast in the fermentate.

Figure 3:
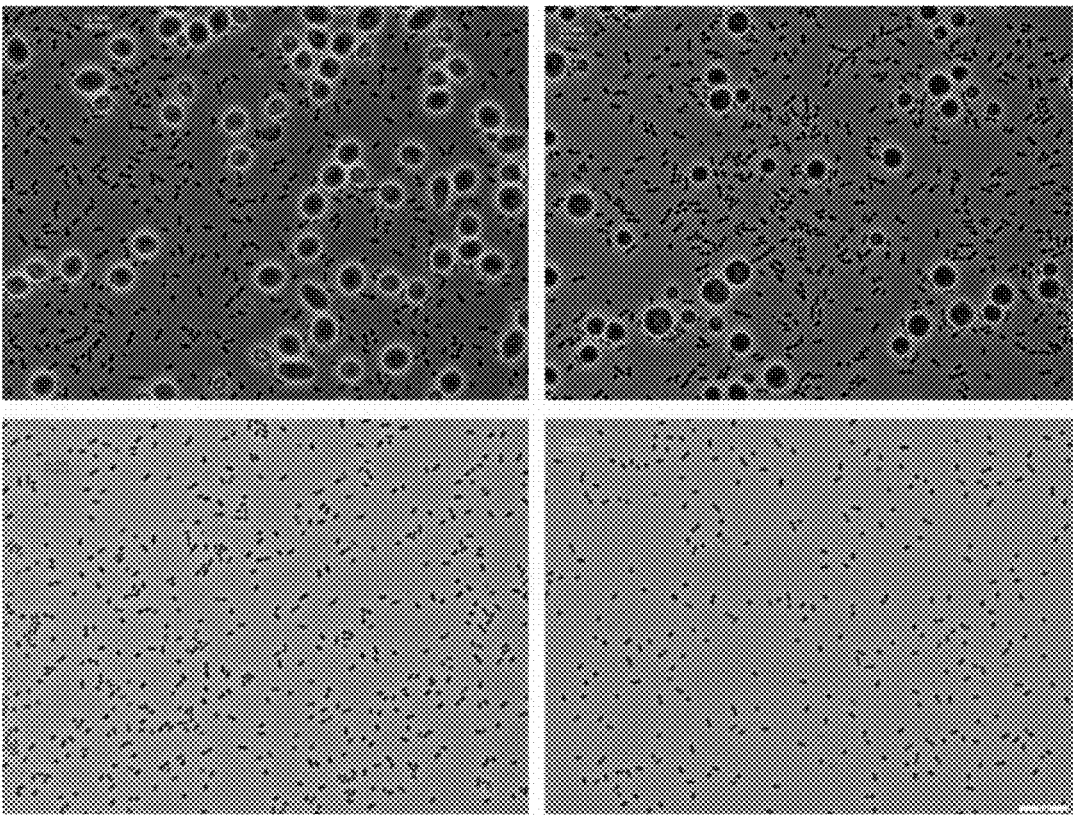

FIG. 3. Microscopy of the *Lactococcus lactis* culture 100× oil objective at end of fermentation with following four processes: Yeast cells as heme source (top; DSM 33527 as representative). Aerobic positive control (bottom left), and Anaerobic negative control (bottom right).

Figure 4:
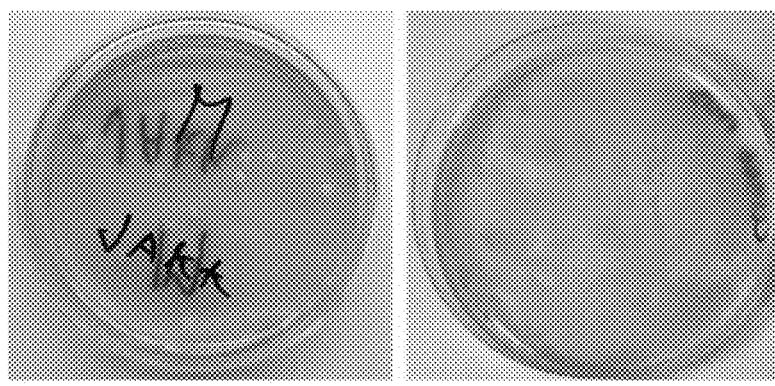

FIG. 4. YGC agar plates after incubation for 4 days at 25° C. On the left a positive control with yeast cells colonies and on the right F-DVS of DSM 33527 as representative. Note no colonies on the latter.

Figure 5:
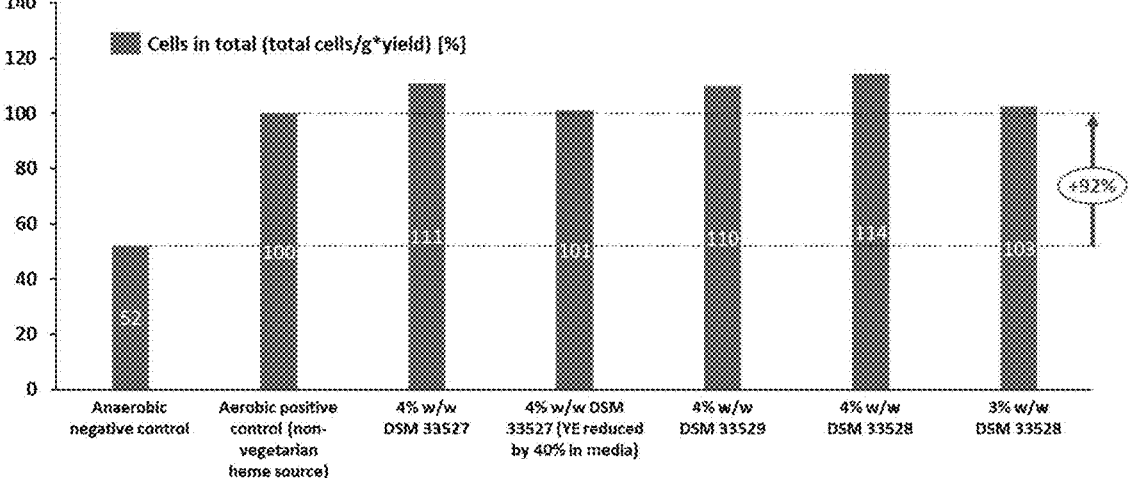
Figure 6A:
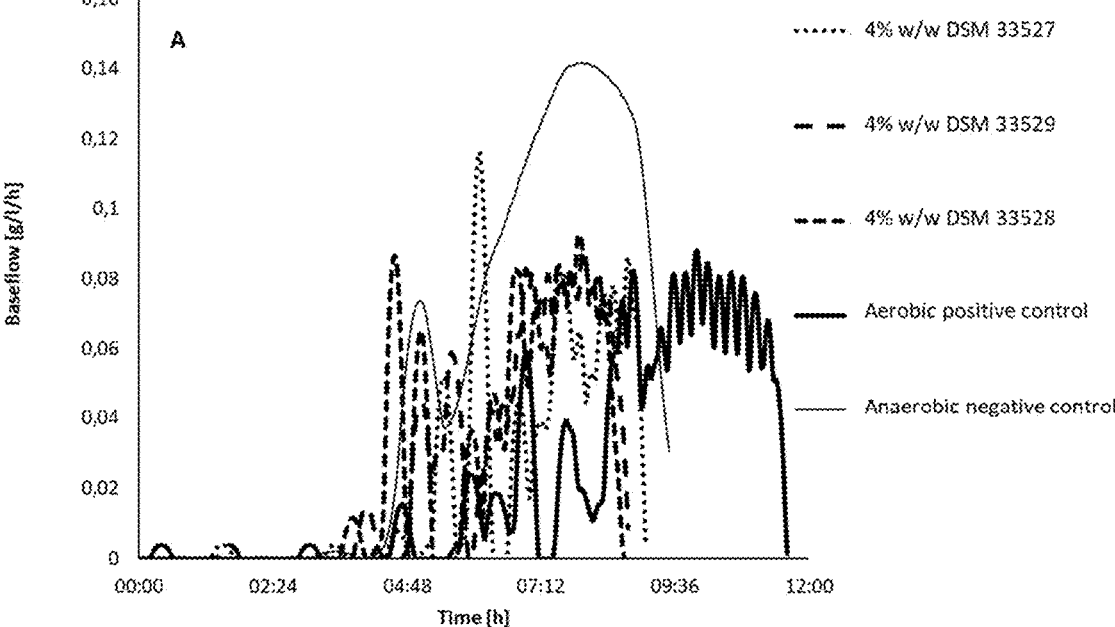
Figure 6B:
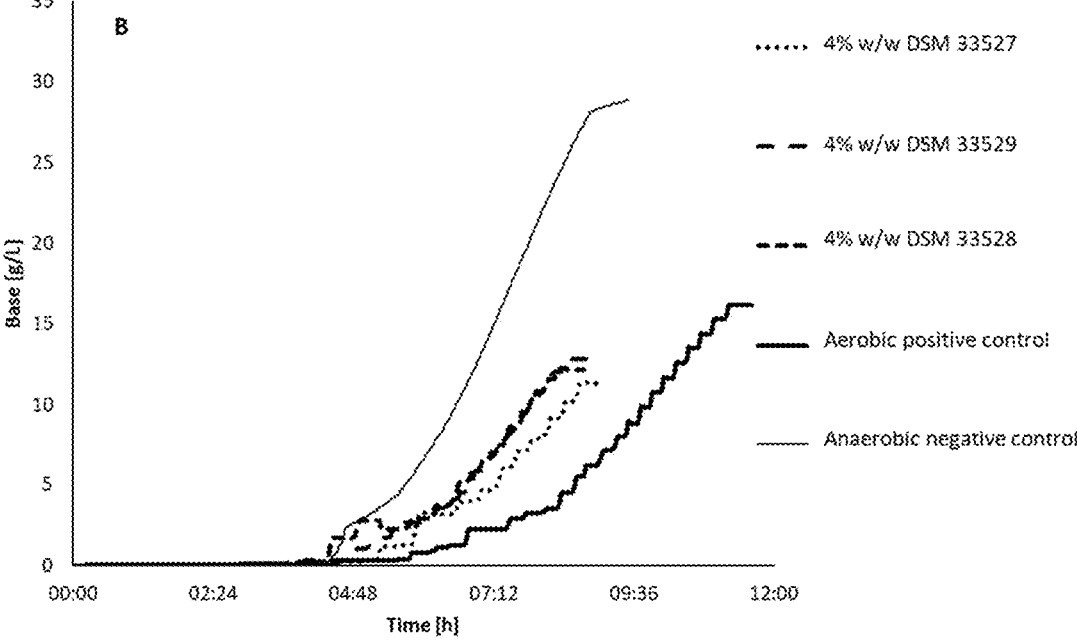
Figure 6C:
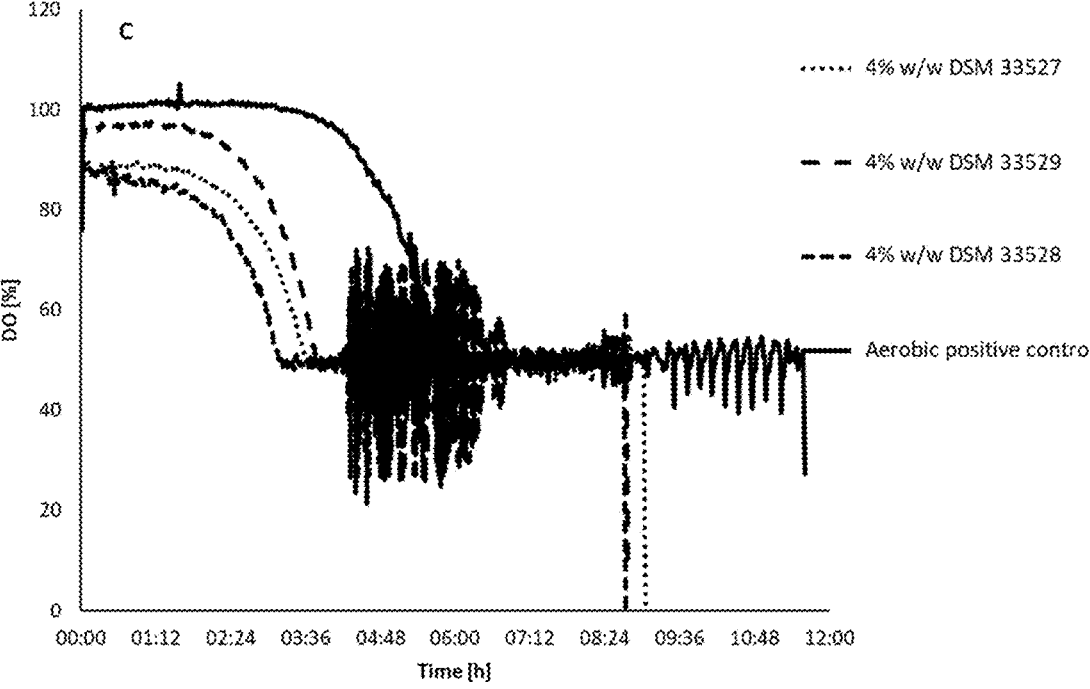
Figure 6D:
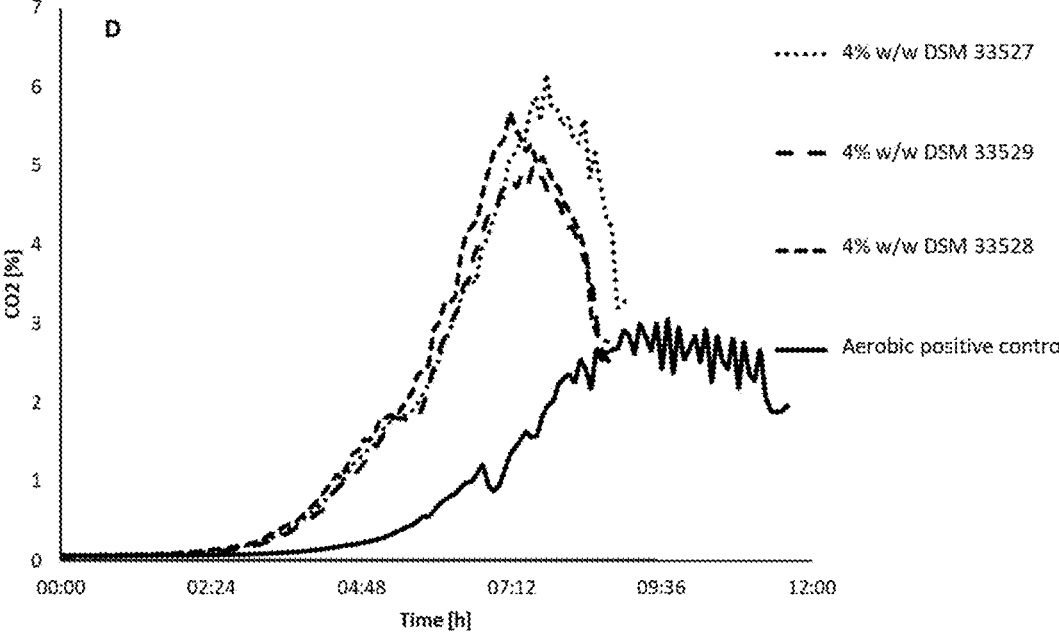

FIG. 5. Comparison of cells in total (total cells/g*yield) produced by respiratory growth using DSM 33527 (4% w/w), DSM 33529 (4% w/w), DSM 33527 (4% w/w) with yeast extract reduction by 40% in media, DSM 33528 (3% and 4% w/w) as well as Aerobic positive control and Anaerobic negative control, the latter being an alternative for a vegetarian process. The values calculated and normalized to the Aerobic positive control process at 100%.

FIGS. 6A-6D. Trend curves of A) Base flow (FIG. 6A), B) Total base used (FIG. 6B), C) Dissolved oxygen (DO %) (FIG. 6C) and D) CO2 (FIG. 6D) for *Lactococcus lactis* during fermentation. The curves are shown respiratory growth with the three yeasts that support respiration, *Torulaspora delbrueckii* (DSM 33529), *Saccharomyces cerevisiae* (DSM 33529) and *Saccharomyces cerevisiae* (DSM 33528) in M17 culture media. Controls are the Aerobic positive control using hemin chloride in M17 media and the Anaerobic negative control in M17 media. The Anaerobic negative control was run with N2 in headspace and therefore without DO probe and off-gas analysis. There are no curves of the Anaerobic negative control in graphs C and D since DO % and CO2 are not measured for this process.

Figure 7:
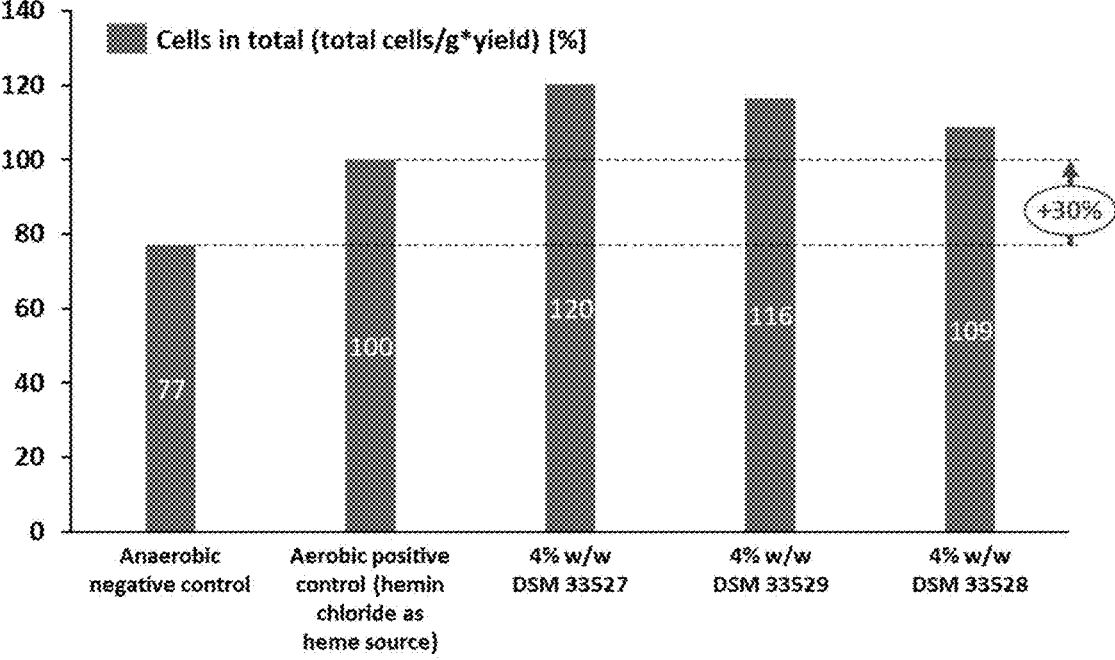

FIG. 7. Comparison of cells in total (total cells/g*yield) produced by respiratory growth using DSM 33527 (4% w/w), DSM 33529 (4% w/w) and DSM 33528 (4% w/w) as well as an Aerobic process using hemin chloride and an anaerobic process as control processes, respectively, in M17 media. The values calculated and normalized to the fermentation process with the Aerobic positive control using hemin chloride at 100%.

ITEMS

1. A method for obtaining a microbial culture, said method comprises the steps of:
   (i) culturing at least one microbial strain in a culture medium under aeration and obtaining a fermentate,
   (ii) harvesting from the fermentate said at least one microbial strain to obtain the microbial culture,
   wherein the culture medium comprises at least one inactivated yeast strain.
2. The method according to item 1, said method further comprising:
   (iii) concentrating the microbial culture to obtain a concentrated microbial culture
3. The method according to any of the preceding items, said method further comprising:
   (iv) freezing said microbial culture to obtain a frozen microbial culture.
4. The method according to any of the preceding items, said method further comprising:
   (v) sublimating water from said frozen microbial culture to obtain a dried microbial culture
5. The method according to item 4, wherein step v) is carried out by a technique selected from the group consisting of spray drying, spray freezing, vacuum drying, air drying, freeze drying, tray drying and vacuum tray drying.

6. The method according to any of the preceding items, said method further comprising:

(vii) packing said frozen microbial culture obtained in step (iv) or the dried microbial culture obtained in step (v).

7. The method according to any of the preceding items, wherein the at least one inactivated yeast strain is a heat inactivated yeast strain.

8. The method according to any of the preceding items, wherein the at least one inactivated yeast strain is a whole yeast cell.

9. The method according to any of the preceding items, wherein the inactivated yeast is a yeast non-culturable when spread on YGC agar plates and incubated at 4 days at 25° C.

10. The method according to any one of the preceding items, wherein the culture medium does not comprises a non-vegetarian compliant heme source.

11. The method according to any one of the preceding items, wherein the culture medium further comprises ingredients selected from the group consisting of peptone, tryptone, yeast extract, magnesium sulphate, ascorbic acid, sugars, vitamins, minerals and combinations thereof.

12. The method according to any of the preceding items, wherein at least one porphyrin compound is present in or is added to the culture medium.

13. The method according to any of the preceding items, wherein at least one yield enhancing agent is present in or is added to the culture medium 14. The method according to item 13, wherein said yield enhancing agent is selected from the group consisting of a purine base, a pyrimidine base, a nucleoside, a nucleotide and derivatives thereof.

15. The method according to item 13, wherein the yield enhancing agent is a purine base 16. The method according to item 15, wherein the purine base is selected from the group consisting of adenine, guanine, xanthine and hypoxanthine 17. The method according to item 13, wherein the yield enhancing agent is a pyrimidine base 18. The method according to item 17, wherein said pyrimidine base is selected from the group consisting of cytosine, thymine and uracil 19. The method according to item 13, wherein the yield enhancing agent is a nucleoside.

20. The method according to item 19, wherein said nucleoside is selected from the group consisting of adenosine, guanosine, uridine, cytidine, inosine, deoxyadenosine, deoxyguanosine, deoxythymidine, deoxycytidine and deoxyinosine.

21. The method according to item 19, wherein said nucleoside is selected from the group consisting of adenosine, guanosine, uridine, cytidine and inosine.

22. The method according to item 13, wherein the nucleoside is inosine.

23. The method according to item 13, wherein said yield enhancing agent is a nucleotide.

24. The method according to item 23, wherein said nucleotide is selected from the group consisting of adenylate (AMP), guanylate (GMP), uridylate (UMP), cytidylate (CMP), xanthylate (XMP), inosinate (IMP), deoxyadenylate (dAMP), deoxyguanylate (dGMP), deoxythymidylate (dTMP), deoxycytidylate (dCMP), deoxyxanthylate (dXMP) and deoxyinosinate (dIMP).

25. The method according to item 23, wherein said nucleotide is selected from the group consisting of AMP, GMP, UMP, CMP, XMP and IMP.

26. The method according to item 23, wherein said nucleotide is IMP.

27. The method according to any of the preceding items, wherein said culture medium comprises at least two yield enhancing agents selected from the group consisting of a purine base, a pyrimidine base, a nucleoside, a nucleotide and derivatives thereof.

28. The method according to item 27, wherein the at least two yield enhancing agents are a nucleoside and a nucleotide.

29. The method according to items 27-28, wherein said nucleoside is inosine and said nucleotide is IMP.

30. The method according to any of the preceding items, wherein the culture medium in step (i) comprises from 1 to 70 mM of each yield enhancing agent.

31. The method according to any of the preceding items, wherein the culture medium in step (i) comprises from 1 to 60 mM of each yield enhancing agent, such as from 1.3 to 60 mM, e.g. from 1.5 to 50 mM, preferably from 2 to 40 mM, such as from 2.5 to 30 mM, e.g. from 3 to 20 mM, more preferably from 3 to 15 mM, such as from 4 to 10 mM, e.g. about 7 mM.

32. The method according to any one of the preceding items, wherein the culture medium in step (i) comprises at least 0.5% w/w of the at least one inactivated yeast stain before fermentation 33. The method according to any one of the preceding items, wherein the culture medium at step (i) comprises at least 0.5% w/w of the at least one microbial strain before fermentation.

34. The method according to any of the preceding items, wherein said high Optical Density conditions are characterized by an $OD_{600}$ above 10 in the culture medium of step (ii)

35. The method according to any of the preceding items, wherein the $OD_{600}$ of the culture medium in step (ii) is in the range from $OD_{600}=10$ to $OD_{600}=200$, more preferably a OD of from $OD_{600}=15$ to $OD_{600}=100$ and most preferably a OD of from $OD_{600}=20$ to $OD_{600}=80$.

36. The method according to any of the preceding items, wherein the culturing is performed in a large scale fermentor comprising from 5 L to 100.000 L culture medium, preferably from 300 L to 20.000 L culture medium.

37. The method according to any of the preceding items, wherein the culturing comprising control of temperature and/or pH.

38. The method according to any of the preceding items, wherein the concentration factor in step (iv) is in the range from 5 to 20.

39. The method according to any of the preceding items, wherein the one or more microbial strain(s) is/are strain(s) microbial strains not capable of respiratory growth without supplementation of components/substitute components of the respiratory chain.

40. The method according to any of the preceding items, wherein the one or more microbial strain(s) is selected from the group consisting of *Bacillus subtilis, Bacillus licheniformis, Bifidobacterium animalis, Bifidobacterium bifidum, Bifidobacterium breve, Bifidobacterium longum, Enterococcus faecium, Lactococcus lactis, Lactobacillus acidophilus, Lactobacillus delbrueckii, Lactobacillus gasseri, Lactobacillus helveticus, Lactobacillus johnsoniim, Lactobacillus animalis (Ligilacto-* bacillus animalis), *Lactobacillus buchneri* (*Lentilacto-bacillus buchneri*), *Lactobacillus curvatus* (*Latilactobacillus curvatus*), *Lactobacillus futsaii* (*Companilactobacillus futsaii*), *Lactobacillus fermentum* (*Limosilactobacillus fermentum*), *Lactobacillus paracasei* (*Lacticaseibacillus paracasei*), *Lactobacillus pentosus* (*Lactiplantibacillus pentosus*), *Lactobacillus plantarum* (*Lactiplantibacillus plantarum*), *Lactobacillus reuteri* (*Limosilactobacillus reuteri*), *Lactobacillus rhamnosus* (*Lacticaseibacillus rhamnosus*), *Lactobacillus* sakei (*Latilactobacillus* sakei), *Lactobacillus salivarius* (*Ligilactobacillus salivarius*), *Leuconostoc carnosum*, *Leuconostoc mesenteroides*, *Leuconostoc pseudomesenteroides*, *Oenococcus oeni*, *Pediococcus acidilactici*, *Pediococcus pentosaceus*, *Propionibacterium freudenreichii*, *Staphylococcus carnosus*, *Staphylococcus vitulinus*, *Staphylococcus xylosus*, *Streptococcus thermophilus* and combinations thereof.

41 The method according to any of the preceding items, wherein the culture medium in step (i) and/or step (ii) comprises one or more mesophilic microorganisms selected from the group consisting of *Lactococcus lactis*, *Lactococcus lactis* subsp. *cremoris*, *Leuconostoc mesenteroides* subsp. *cremoris*, *Pediococcus pentosaceus*, *Lactococcus lactis* subsp. *lactis* biovar. *diacetylactis*, *Lactobacillus casei* subsp. *casei* (*Lacticaseibacillus casei*), *Lactobacillus paracasei* subsp. *paracasei* (*Lacticaseibacillus paracasei* subsp. *paracasei* and *Lacticaseibacillus paracasei* subsp. *tolerans*), *Oenococcus oeni* and combinations thereof.

42. The method according to any of the preceding items, wherein the culture medium in step (i) and/or step (ii) comprises one or more thermophilic microorganisms having optimum growth temperatures at about 40° C. to about 45° C.

43. The method according to any of the preceding items, wherein the culture medium in step (i) and/or step (ii) comprises one or more thermophilic microorganisms selected from the group consisting of *Streptococcus thermophilus*, *Enterococcus faecium*, *Lactobacillus delbrueckii* subsp. *lactis*, *Lactobacillus helveticus*, *Lactobacillus delbrueckii* subsp. *Bulgaricus*, *Lactobacillus acidophilus* and combinations thereof.

44. The method according to any of the preceding items, wherein the culture medium in step (i) and/or step (ii) is an LD-culture that comprises one or more microorganisms selected from the group comprising *Lactococcus lactis* subsp. *lactis*, *Lactococcus lactis* subsp. *cremoris*, *Lactococcus lactis* subsp. *lactis* biovar. *diacetylactis* and *Leuconostoc mesenteroides* subsp. *cremoris*.

45. The method according to any of the preceding items, wherein the culture medium in step (i) and/or step (ii) is an O-culture that comprises one or more organisms selected from the group comprising *Lactococcus lactis* subsp. *lactis* and *Lactococcus lactis* subsp. *cremoris*.

46. The method according to any of the preceding items, wherein the culture medium in step (i) and/or step (ii) is a culture comprising *Lactococcus lactis*.

47. The method according to any of the preceding items, wherein the at least one yeast strain is selected from the group consisting of *Torulaspora delbrueckii*, *Saccharomyces cerevisiae*, *Pichia kluyveri*, *Debaromyces hansenii*, *Lachancea thermotolerans*, *Torula* Yeast and combinations thereof.

48. The method according to any of the preceding items, wherein the at least one yeast strain is selected from the group consisting of *Torulaspora delbrueckii*, *Saccharomyces cerevisiae* and combinations thereof.

49. The method according to any of the preceding items, wherein the at least one inactivated yeast strain. is selected from the group consisting of *Torulaspora delbrueckii* deposited as DSM 33529, *Saccharomyces cerevisiae* deposited as DSM 33527, *Saccharomyces cerevisiae* deposited as DSM 33528 and combinations thereof.

50. The method according to any of the preceding items, wherein at least one cryoprotectant is added to the harvested lactic acid bacteria culture obtained in step (ii) or to the concentrated lactic acid bacterial culture obtained in step (iii)

51. The method according to any one of the preceding items, wherein culture is aerated so as to maintain, during the whole duration of the culture, an oxygen content which is equal to at least 5 millimoles per litre of culture medium 52. The method according to any one of the preceding items, wherein the harvest in step (ii) is performed between 5 to 24 hours after the start of the culture 53. The method according to any one of the preceding items, wherein the method further comprises storage of the harvested lactic acid bacteria culture obtained in step (ii) or the concentrated lactic acid bacteria culture obtained in step (iii)

54. The method according to any of the preceding items, wherein the fermentate obtained in step (i) comprises in the range of 2.0E+10-5.0E+10 active microbial cells/g culture 55. The method according to any of the preceding items, wherein the fermentate obtained in step (i) comprises in the range of 2.0E+10-5.0E+10 total microbial cells/g culture 56. The method according to any of the preceding items, wherein the yield is increased by a factor of at least 1.2 when compared to the yield obtained by identical process applying a non-vegetarian compliant heme source.

57. A culture obtainable by the method according to any of items 1-56

58. A culture according to item 56, wherein the culture is a starter culture.

59. The culture according to item 57, wherein the starter culture is provided as a starter culture concentrate.

60. A culture comprising at least one inactivated yeast strain.

61. A culture according to item 60, wherein the culture is a starter culture.

62. The culture according to item 61, wherein the at least one inactivated yeast strain is a whole yeast cell.

63. The culture according to any one of items 61 or 62, wherein the at least one inactivated yeast strain is selected from the group consisting of *Torulaspora delbrueckii* deposited as DSM 33529, *Saccharomyces cerevisiae* deposited as DSM 33527, *Saccharomyces cerevisiae* deposited as DSM 33528 and combinations thereof.

64. A culture medium comprising at least one inactivated yeast strain.

65. The culture medium according to item 64, wherein the at least one inactivated yeast strain is a whole yeast cell.

66. The culture medium according to item 64, wherein the at least one inactivated yeast strain is selected from the group consisting of *Torulaspora delbrueckii* deposited as DSM 33529, *Saccharomyces cerevisiae* deposited as DSM 33527,
*Saccharomyces cerevisiae* deposited as DSM 33528 and combinations thereof.

67. The culture medium according to item 64, wherein said medium is as defined in any of the preceding claims 68. A method of preparing a food product, feed product, a pharmaceutical product, a dairy flavor and a cheese flavoring product, said method comprising adding an effective amount of the culture according to items 57-63 to a food, feed or pharmaceutical product starting material and keeping the inoculated culture under conditions where the at least one microbial strain is metabolically active.

69. A method according to item 68, wherein the food product is selected from the group consisting of a milk-based product, a vegetable product, a meat product, a beverage, a fruit juice, a wine and a bakery product 70. A method according to item 69, wherein the milk-based product is selected from the group consisting of a cheese, a yoghurt, a butter, an inoculated sweet milk and a liquid fermented milk product 71. A fermented food, feed or pharmaceutical product obtainable by the method of any of items 1-56

72. Use of at least one inactivated yeast strain in a fermentation method and/or a fermentation process.

73. The use according to item 72, wherein the at least one inactivated yeast strain is selected from the group consisting of *Torulaspora delbrueckii* deposited as DSM 33529, *Saccharomyces cerevisiae* deposited as DSM 33527, *Saccharomyces cerevisiae* deposited as DSM 33528 and combinations thereof.

74. A food product, feed product, a pharmaceutical product, a dairy flavor and a cheese flavoring product, comprising the culture according to any one of items 57-63.

EXAMPLES

Example 1: Yield from Fermentations in a Complex Fermentation Medium of Chr Hansen A/S Performed with Different Types of Yeasts as Heme Source Overview of Yeasts Tested for their Ability to Support Respiratory Growth:

Eleven different yeasts (Table 1) was tested as an alternative vegetarian heme source for their ability to support respiration of *Lactococcus lactis*. Three yeasts were able to support respiration: *Torulaspora delbrueckii* (DSM 33529), *Saccharomyces cerevisiae* (DSM 33527) and *Saccharomyces cerevisiae* (DSM 33528).

TABLE 1

Overview of yeasts that have been tested for their ability to support respiratory
growth of *Lactococcus lactis*. All yeasts are added to fermentation media.

| Material description | Yeast Strain | Support respiratory growth |
|---|---|---|
| DSM 33529 | *Torulaspora delbrueckii* | Yes |
| DSM 33527 | *Saccharomyces cerevisiae* | Yes |

TABLE 1-continued

Overview of yeasts that have been tested for their ability to support respiratory
growth of *Lactococcus lactis*. All yeasts are added to fermentation media.

| Material description | Yeast Strain | Support respiratory growth |
|---|---|---|
| DSM 33528 | *Saccharomyces cerevisiae* | Yes |
| FLY-DVS DIBS | *Saccharomyces cerevisiae* | Yes |
| Malteserkors Tørgær * | *Saccharomyces cerevisiae* | No |
| Inactivated Yeast NuCel 510 | Inactivated *Saccharomyces cerevisiae* | No |
| F-DVS @NEER | *Pichia kluyveri* | No |
| F-DVS Viniflora FrootZen | *Pichia kluyveri* | No |
| SWING LAF-3 | *Debaromyces hansenii* | No |
| Viniflora ® CONCERTO | *Lachancea thermotolerans* | No |
| Yeast Extract Provesta | *Torulaspora delbrueckii* Yeast | No |

\* This raw material is an indication that not all *Saccharomyces cerevisiae* strains could support the respiration Culture:

The present experiment was performed using the commercially available DSM 24648 culture, which is available from Chr. Hansen A/S, Hoersholm, Denmark.

Fermentation Medium:

Three different fermentation media was used in Example 1:

1—A proprietary vegetarian friendly complex fermentation medium of Chr Hansen A/S was applied including different types of Yeasts as heme source 2—An anaerobic complex fermentation medium was used as medium for negative control. The medium was proprietary vegetarian friendly complex fermentation medium of Chr Hansen A/S not including a heme source.

3—An aerobic complex fermentation medium was used as medium for positive control.

The medium was proprietary vegetarian friendly complex fermentation medium of Chr Hansen A/S including a non-vegetarian heme source.

The medium was sterilized by UHT-treatment (143° C. for 8 sec.). The finished medium had a pH of 6.5.

Fermentation Condition the Cultures

The fermentation was performed in a 2 L Lab scale fermentation tank with aeration at 30° C. using 1% (w/w) of the culture mentioned above as inoculum and one of the abovementioned inactivated yeast as heme source. For aerobic fermentation as a positive control, the same conditions as for the aerobic fermentation was applied with aeration in a proprietary vegetarian friendly complex fermentation medium of Chr Hansen A/S including a non-vegetarian heme source. For anaerobic fermentation as a negative control, the same conditions as for the aerobic fermentation was applied but without aeration in a proprietary vegetarian friendly complex fermentation medium of Chr Hansen A/S excluding heme source. The cultures were allowed to acidify to pH 6.0. The pH was subsequently maintained at 6.0 by controlled addition of 27% $NH_4OH$.

When no further base consumption was detected, the respective culture was cooled down to about 10° C.

Following cooling, the bacteria in the culture media were concentrated 6-18 times by centrifugation and subsequently frozen as pellets in liquid nitrogen at one atmosphere of pressure to produce a so-called frozen Direct Vat Set culture (F-DVS). The F-DVS pellets were stored at −50° C. until further analysis The yields of the fermentations were specified in two different ways:

1. by the obtained biomass measured as the Optical Density at 600 nm ($OD_{600}$), or
2. by kg of F-DVS culture pr. 100 L fermentation medium wherein the F-DVS culture have an "acidification activity" of 4.8-5.1 according to the Pearce test described in Example 3: Analytical Procedure QAm-043.

Process Parameters Evaluation

*Lactococcus lactis* changes metabolism profoundly when going from anaerobic to respiratory growth. Compared to anaerobic growth, biomass is approximately doubled, and acid production is reduced during respiratory growth. The reduction in acid production is apparent from the base flow (amount of base used per volume per time) and total base used to keep a specified pH setpoint during fermentation. It is clearly visible that base consumption is much higher for the anaerobic process (control) (FIG. 1A, B). Respiratory fermentation processes using DSM 33529 (4% w/w), DSM 33527 (4% w/w) and DSM 33527 (4% w/w and reduction of yeast extract in the media by 40%) as a heme source showed similar base flow and the total base curves compared to the Aerobic positive control (i.e. a respiratory fermentation process with a non-vegetarian source as heme source).

Another key feature of respiratory growth is the reduction of dissolved oxygen (DO %) and production of $CO_2$ (FIG. 1 C,D). Compared to the Aerobic positive control, the respiratory fermentation process using DSM 33529 (4% w/w), DSM 33527 (4% w/w) and DSM 33527 (4% w/w and reduction of yeast extract in the media by 40%) showed similar dissolved oxygen (DO %) and production of $CO_2$ profiles (FIG. 1 C, D). The anaerobic growth reference, the Anaerobic negative control process, is not included in FIG. 1 C, D as this process was run with nitrogen in the head-space.

As a conclusion, based on the process curves in FIG. 1, respiratory fermentation process using DSM 33529, DSM 33527 and DSM 33528 performed as good as the Aerobic positive control (FIG. 1, non-vegetarian heme source) to support respiratory growth.

Furthermore, FIG. 1 shows that the fermentation process with reduced yeast extract from media containing DSM 33527 also support respiratory growth indicating that yeast cells and not the yeast extract is supporting respiration.

Downstream Process Evaluation

After fermentation, a packed cell volume (PCV) test is done on the fermentate (centrifugation of the fermentate in special centrifuge tubes). This is the first indication of biomass. The PCV test show that fermentation with DSM 33529, DSM 33527 and DSM 33528 resulted in the same level of bacterial cells at 10% PCV as the Aerobic positive control process whereas the Anaerobic negative control resulted in a lower level of 4% PCV (FIG. 3). Though the level of bacteria for DSM 33529, DSM 33527 and DSM 33528 correlates to Aerobic positive control, the three first-mentioned also showed a level of 10% PCV from yeast cells (Beige color layer in the bottom). Appearance of the final product (F-DVS) showed no difference to the reference Aerobic positive control process (FIG. 2). The color of pellets are white/beige white pellets.

Microscopy at the End of Fermentation

The use of yeast in the fermentation media is also evident in the microscopy pictures (FIG. 3).

Culturability of Yeast Cells after Fermentation

To ensure that there were no culturable yeast cells in the end-product (F-DVS), it was spread on YGC agar plates. No growth was observed for any of the trials described here (FIG. 4).

Summary of Respiratory Growth Performance with Yeast Cells as an Alternative Vegetarian Raw Material Instead of Non-Vegetarian Compliant Heme Source An overview of process responses (fermentation time, base consumption and OD) and analytical results (active and total amounts of cells and acidification activity (Ta)) for the fermentate, concentrate and F-DVS products is given in Table 2. In FIG. 5 the cells in total (total cells/g*yield) is presented which is the key feature calculated from Table 2 and it has been normalized to the Aerobic positive control process at 100% (FIG. 5). As it can be seen in Table 2 and FIG. 5, the respiratory processes with yeasts correlates very well with the Aerobic positive control yield which doubled the yield compared to Anaerobic negative control. The reduction of yeast extract in the media by 40% did not affect the respiratory growth yield confirming that the increase in yield is due to respiration and not increased nitrogen content in media.

TABLE 2

Batch overview of selected fermentations runs with DSM 33527, DSM 33529, DSM 33528, Aerobic positive control and Anaerobic negative control including fermentation responses and analytical results.

| Process | | Anerobic negative control | Aerobic positive control | DSM 33527 (4% w/w) | DSM 33527 (4% w/w) & YE reducion by 40% in media | DSM 33529 (4% w/w) | DSM 33528 (4% w/w) | DSM 33528 (3% w/w) |
|---|---|---|---|---|---|---|---|---|
| Heme source | | NA-anaerobic | Non-vegetarian source | Yeast: *Saccharomyces cerevisiae* | Yeast: *Saccharomyces cerevisiae* | Yeast: *Torulaspora delbrueckii* | Yeast: *Saccharomyces cerevisiae* | Yeast: *Saccharomyces cerevisiae* |
| Respiratory growth | | No | Yes | Yes | Yes | Yes | Yes | Yes |
| Fermentate | Fermentation time | 8.75 | 9.08 | 8.42 | 7.4 | 9.22 | 7.50 | 7.00 |
| | Base consumption g/L | 30.29 | 19.4 | 15.3 | 17.67 | 17.58 | 9.27** | 8.13** |

TABLE 2-continued

Batch overview of selected fermentations runs with DSM 33527, DSM 33529, DSM
33528, Aerobic positive control and Anaerobic negative control including fermentation
responses and analytical results.

| | Process | Anerobic negative control | Aerobic positive control | DSM 33527 (4% w/w) | DSM 33527 (4% w/w) & YE reducion by 40% in media | DSM 33529 (4% w/w) | DSM 33528 (4% w/w) | DSM 33528 (3% w/w) |
|---|---|---|---|---|---|---|---|---|
| | OD (end of fermentation) | 19.2 | 36.1 | 29.44 | 29.28 | 28.56 | 29.36 | 31.04 |
| | Active cells/g | 2.40E+10 | 4.13E+10 | 3.92E+10 | 4.06E+10 | 3.43E+10 | 3.16E+10 | 3.16E+10 |
| | Total cells/g | 2.44E+10 | 4.18E+10 | 4.17E+10 | 4.21E+10 | 3.66E+10 | 3.45E+10 | 3.33E+10 |
| Concen-trate | Concentration factor | 10.76 | 10 | 6.48 | 5.55 | 5.34 | 6.2 | 6.3 |
| F-DVS | Active cells/g | 2.45E+11 | 4.38E+11 | 2.99E+11 | 2.33E+11 | 2.43E+11 | 2.05E+11 | 1.99E+11 |
| | Total cells/g | 2.58E+11 | 4.60E+11 | 3.32E+11 | 2.58E+11 | 2.71E+11 | 2.28E+11 | 2.08E+11 |
| | YIELD %*** | 10.69 | 11.50 | 17.75 | 20.72 | 21.54 | 18.55 | 18.25 |

*Yield calculated as 100% divided by concentration factor and adjusted for cryo addition
**Low values of Base consumption are due to less sugar addition to growth media
***The acidification activity of the F-DVS is 4.8-5.2 according to the Pearce test (Example 3)

Example 2: Yield from Fermentations in M17 Medium and Performed with Different Types of Yeasts as Heme Source Overview of Yeasts Tested for their Ability to Support Respiratory Growth:

Eleven different yeasts (Table 1) were tested as alternative vegetarian heme sources—i.e. for their ability to support respiration of *Lactococcus lactis*. Three yeasts were able to support respiration: *Torulaspora delbrueckii* (DSM 33529), *Saccharomyces cerevisiae* (DSM 33527) and *Saccharomyces cerevisiae* (DSM 33528).

TABLE 3

Overview of yeasts that have been tested for their ability
to support respiratory growth of *Lactococcus lactis*.
All yeasts are added to fermentation media.

| Material description | Yeast Strain | Support respiratory growth |
|---|---|---|
| DSM 33529 | *Torulaspora delbrueckii* | Yes |
| DSM 33527 | *Saccharomyces cerevisiae* | Yes |
| DSM 33528 | *Saccharomyces cerevisiae* | Yes |
| FLY-DVS DIBS | *Saccharomyces cerevisiae* | Yes |
| Malteserkors Tørgær * | *Saccharomyces cerevisiae* | No |
| Inactivated Yeast NuCel 510 | Inactivated *Saccharomyces cerevisiae* | No |
| F-DVS @NEER | *Pichia kluyveri* | No |
| F-DVS Viniflora FrootZen | *Pichia kluyveri* | No |
| SWING LAF-3 | *Debaromyces hansenii* | No |
| Viniflora ® CONCERTO | *Lachancea thermotolerans* | No |
| Yeast Extract Provesta | *Torulaspora delbrueckii* | No |

* This raw material is an indication of not all *Saccharomyces cerevisiae* strains could support the respiration Culture:

The present experiment was performed using the commercially available DSM 24648 culture, which is available from Chr. Hansen A/S, Hoersholm, Denmark.

Fermentation Medium:
1. The cultures were cultured in commercially available M17 medium having the following composition: Tryptone (casein digest by trypsin), 5 g/L; Soya peptone, 5 g/L; Lab-lemco powder, 5 g/L; Yeast extract, 2.5 g/L; Ascorbic acid 0.5 g/L; Magnesium sulphate, 0.25 g/L; and Lactose, 40 g/L The same medium composition of M17 was used for fermentations with Yeast as a heme source, Aerobic positive control (wherein hemin chloride (Sigma Aldrich) was used as a heme source) and Anaerobic negative control (without a heme source).

The medium was sterilized by UHT-treatment (143° C. for 8 sec.). The finished medium had a pH of 6.5.

Fermentation Condition the Cultures:

The fermentation was performed in a 2 L Lab scale fermentation tank with aeration at 30° C. using 1% (w/w) of the culture mentioned above as inoculum and one of the abovementioned inactivated yeast as a heme source. For aerobic fermentation as the positive control, the same conditions as for aerobic fermentation was applied with aeration in M17 medium including hemin chloride as a heme source. For anaerobic fermentation as a negative control, the same conditions as for the aerobic fermentation was applied but without aeration in M17 medium not including a heme source. The cultures were allowed to acidify to pH 6.0. The pH was subsequently maintained at 6.0 by controlled addition of 27% $NH_4OH$.

When no further base consumption was detected, the respective culture was cooled down to about 10° C.

Following cooling, the bacteria in the culture media were concentrated 6-18 times by centrifugation and subsequently frozen as pellets in liquid nitrogen at one atmosphere of pressure to produce a so-called frozen Direct Vat Set culture (F-DVS). The F-DVS pellets were stored at −50° C. until further analysis The yields of the fermentations were specified in two different ways:
 by the obtained biomass measured as the Optical Density at 600 nm (OD600), or
 by kg of F-DVS culture pr. 100 L fermentation medium wherein the F-DVS culture have an "acidification activity" of 4.8-5.1 according to the Pearce test described in Example 3: Analytical Procedure QAm-043.

Process Parameters Evaluation

*Lactococcus lactis* changes metabolism profoundly when going from anaerobic to respiratory growth. Compared to anaerobic growth, biomass is approximately doubled, and acid production is reduced during respiratory growth. The reduction in acid production is apparent from the base flow (amount of base used per volume per time) and total base used to keep a specified pH setpoint during fermentation.

The respiratory fermentation process using DSM 33529 (4% w/w), DSM 33527 (4% w/w) and DSM 33528 (4% w/w) as heme source in M17 media (FIG. 6A, B) showed similar base flow and total base curves compared to Aerobic positive control.

In FIG. 6 C, D, respiratory fermentation process using DSM 33529 (4% w/w), DSM 33527 (4% w/w) and DSM 33528 (4% w/w) was performed in M17 media. Compared with the Aerobic positive control similar dissolved oxygen (DO %) and production of $CO_2$ profiles was obtained using DSM 33529 (4% w/w), DSM 33527 (4% w/w) and DSM 33528 (4% w/w) (FIG. 6 C, D). The anaerobic growth reference (Anaerobic negative control) is not included since it is run with nitrogen in the headspace.

As a conclusion, based on the process curves in FIG. 6, respiratory fermentation process using DSM 33529, DSM 33527 and DSM 33528 performed as good as Aerobic positive control in FIG. 6 (control fermentation using hemin chloride as heme source)) to support respiratory growth.

Summary of Respiratory Growth Performance with Yeast Cells as an Alternative Vegetarian Raw Material Instead of Hemin Chloride as a Heme Source An overview of process responses (fermentation time, base consumption and OD) and analytical results (active and total amounts of cells and acidification activity (Ta)) for fermentate, concentrate and F-DVS products is given in Table 4. In FIG. 7 the cells in total (total cells/g*yield) is presented which is the key feature calculated from Table 4. Also it has been normalized to the fermentation process with hemin chloride (Aerobic positive control) (FIG. 7). As it can be seen in Table 4 and FIG. 7, the respiratory processes with yeasts correlates very well with the Aerobic positive control yield with significant yield increase compared to the Anaerobic negative control.

Example 3: Analytical Procedure QAm-043, Acidification Activity—"Programmed Temperature Profile" Chr. Hansen A/S (Denmark)

Application

This method is used for determination of acidification activity according to Pearce test. The Pearce test is included by the IDF standard (international dairy standard).

Principle

The acidification is performed according to a temperature profile reflecting the temperature course, which the culture will typically encounter when used in the dairy for production of a given dairy product.

For Pearce test this is the cheese making temperature during the production of Cheddar.

pH is measured at a fixed time.

For cultures where rennet is not added during analysis, a continuous pH measurement may be applied.

Analysing Parameters

Analyzing parameters, which are product specific, are given in LIMS.

Definition of temperature profile (for products where Pearce profile is not used).

Control standard to be used.

Type of pH measurement.

Inoculation percents for sample and control standards.

Dilution milk: 206.9 g cold (4° C.) LAB-milk (i.e. UHT-sterilized reconstituted skimmed milk (RSM) containing 9.5% (w/w) solid matter and heated at 99° C. for 30 minutes).

Activity milk: 200 g cold (4° C.) low pasteurized whole milk 3.5% fat.

Rennet: Naturén® standard 190 diluted 1:40 with water.

Apparatus and Reagents pH meter/pH meter for semi continuously pH measurement eks. Radiometer® PHM92.

pH electrode Radiometer® PFC2401.

Buffers: pH 7.00±0.01 and pH 4.01±0.01.

Water bath with a thermostat programmed for heating according to a predetermined temperature profile±0.2° C.

Temperature sensor.

Balance, precision 0.01 g with minimum two decimals

Watch.

TABLE 4

Batch overview of fermentation run in M17 media with DSM 33527, DSM 33529DSM 33527, DSM 33528, Hemin chloride and Anaerobic including fermentation responses.

| | Process | Anaerobic negative control | Aerobic positive control | DSM 33527 4% w/w | DSM 33529 4% w/w | DSM 33528 4% w/w |
|---|---|---|---|---|---|---|
| | Heme source | NA-anaerobic | Hemin Chloride | Yeast: *Saccharomyces cerevisiae* | Yeast: *Saccharomyces cerevisiae* | Yeast: *Torulaspora delbrueckii* |
| | Respiratory growth | No | Yes | Yes | Yes | Yes |
| Fermentate | Fermentation time | 13 | 11.77 | 9.25 | 8.97 | 9 |
| | Base consumption g/L | 31 | 16 | 11 | 13 | 12 |
| | OD (end of fermentation) | 16 | 18 | 7 | 11 | 8 |
| | Active cells/g | 2.59E+10 | 3.11E+10 | 3.76E+10 | 3.60E+10 | 3.54E+10 |
| | Total cells/g | 2.67E+10 | 3.50E+10 | 3.97E+10 | 3.96E+10 | 4.10E+10 |
| Concentrate | Concentration factor | 5 | 5 | 5 | 5 | 5 |
| F-DVS | Active cells/g | 1.55E+11 | 1.85E+11 | 2.25E+11 | 2.17E+11 | 2.13E+11 |
| | Total cells/g | 1.69E+11 | 2.19E+11 | 2.63E+11 | 2.55E+11 | 2.38E+11 |
| | YIELD %* | 20 | 20 | 20 | 20 | 20 |

*Yield calculated as 100% divided by concentration factor and adjusted for cryo addition
*The acidification activity of the F-DVS is 4.8-5.2 according to the Pearce test (Example 3)

Magnetic stirrer.

Magnets

Beakers, 50 ml.

Small plastic cups.

Rotation apparatus.

Procedure

Preparation of Analysis

All bottles should be from the same batch i.e. with the same date.

Water bath/s is/are tempered to the initial temperature of the temperature profile to be used.

Bottles for dilution (=first weighing) and for activity (second weighing) are placed at 4° C. until just before use.

Buffers pH 4.01 and pH 7.00 are placed in water bath at the specified measuring temperature±0.2° C. at least 30 min before calibration of pH meter.

Preparation of Samples Before Analysis.

Frozen Cultures:

Frozen samples/control standards are before first weighing placed in a foam box with dry ice and are kept here till all weighings are done.

Frozen Cultures, which are Thawed Before Use:

For frozen products, where a whole carton is used, the product is thawed according to current instructions.

After thawing the sample may be kept at 4° C. for max. 30 min, before use.

Freeze Dried Cultures:

Freeze dried samples and control standards are acclimatized at room temperature for at least 15 min before start of analysis.

Provided that the sample are going to be used for retest the day after, it may be stored at +8° C.

Inoculation Procedure:

Weighing of product/control standard is carried out directly into the milk.

The actual amount of inoculum (1st weighing) is entered with at least two decimals.

Frozen and thawed products are turned carefully about 4 times, after which the bottle stands for approx. 50 sec.

For freeze dried products the rotation apparatus must be used. It has to be driven with frequent speed for 5 minutes or till the product is completely dissolved. This is controlled by leaving the bottle on the table for a moment and then checking the solution by looking in the bottom of the bottle.

Note:

If convenient for the working routine a cold, first weighing can stand at room temperature for max. 15 minutes before second weighing.

2nd Weighing:

The dilution bottle is turned before 2. weighing is carried out.

The actual amount of inoculum (2nd weighing) is entered with at least 2 decimals.

The activity bottle is turned and the inoculation procedure is repeated for samples/control standards.

Activity bottles, which are inoculated from the same 1st weighing, are inoculated in succession.

2 ml rennet is added each bottle either before or after 2. weighing. After this the bottles are turned so the rennet has been distributed.

The bottles are subsequently incubated at one time, as described in 6.

In the end 2 uninoculated milk bottles are placed in a water bath; one for measuring of the water bath temperature and one for measuring pH in the blind milk.

Incubation

Note: When more water baths are required, the control standard with corresponding samples MUST be incubated in the same water bath.

All activity bottles are incubated at the same time in a pre-heated water bath at the defined starting temperature for the temperature profile.

The temperature profile is started at the same time as the bottles are placed in the water bath.

Hereafter the incubation temperature is controlled by a thermostat programmed for following a certain temperature profile. For Pearce test see table 4.

The water level in the water bath should be min. 2 cm higher than the surface of the milk.

TABLE 5

| Temperature program in Pearce profile (following the IDF) | | |
|---|---|---|
| Time, minutes | Temperature,° C. | Variation |
| 0 | 31.0 | ±0.2° C. |
| 50 | 31.0 | ±0.2° C. |
| 54 | 31.7 | ±0.5° C. |
| 58 | 32.2 | ±0.5° C. |
| 62 | 32.8 | ±0.5° C. |
| 66 | 33.3 | ±0.5° C. |
| 70 | 33.9 | ±0.5° C. |
| 73 | 34.4 | ±0.5° C. |
| 76 | 35.0 | ±0.5° C. |
| 79 | 35.6 | ±0.5° C. |
| 82 | 36.1 | ±0.5° C. |
| 85 | 36.7 | ±0.5° C. |
| 87.5 | 37.2 | ±0.5° C. |
| 90 | 37.8 | ±0.2° C. |
| 360 | 37.8 | ±0.2° C. |

Calibration of pH Electrode

Calibration is carried out at initial temperature according to current instructions regarding electrode calibration and maintenance.

Measurement of pH

After incubation the bottles are shaken well and pH is measured.

The pH measurement is carried out in the bottle or in a sample, which is poured into a 50 ml beaker with magnet stirring.

pH is entered with at least 2 decimals.

Possible remarks on the measurement are entered.

The measuring procedure is continued till all samples/control standards and the uninoculated milk are measured.

Finally pH in buffers are measured and entered.

Continuous pH Measurement

The pH values are sampled from the moment, the temperature profile is started. After the incubation is completed, the measured pH values in both buffers at initial temperature are registered.

REFERENCES

Mogensen et al. (2002) Bulletin of the IDF No. 377, 10-19

Zeng et al. 2020, A taxonomic note on the genus *Lactobacillus*: Description of 23 novel genera, emended description of the genus *Lactobacillus* Beijerinck 1901, and union of Lactobacillaceae and Leuconostocaceae, International Journal of Systemic and Evolutionary Microbiology; Volume 70; Issue 4.

The invention claimed is:

1. A method for obtaining a vegetarian-compliant microbial culture, said method comprising the steps of:
    (i) culturing a microbial strain in a culture medium under aeration to obtain a fermentate,
    (ii) harvesting the microbial strain from the fermentate to obtain the microbial culture;
    wherein the culture medium comprises an inactivated yeast strain;
    wherein the culture medium does not comprise a non-vegetarian heme source; and
    wherein the inactivated yeast strain is in the form of lysed yeast cell extract.

2. The method according to claim 1, said method further comprising:
    (iii) concentrating the microbial culture to obtain a concentrated microbial culture.

3. The method according to claim 2, said method further comprising:
    (iv) freezing said microbial culture to obtain a frozen microbial culture.

4. The method according to claim 3, said method further comprising:
    (v) sublimating water from said frozen microbial culture to obtain a dried microbial culture.

5. The method according to claim 4, said method further comprising:
    (vii) packing said frozen microbial culture obtained in step (iv) or the dried microbial culture obtained in step (v).

6. The method according to claim 1, wherein the at least one inactivated yeast strain is a heat inactivated yeast strain.

7. The method according to claim 1, wherein the inactivated yeast strain is one or more selected from *Torulaspora delbrueckii* deposited at Deutsche Sammlung von Mikroorganismen und Zellkulturen GmbH (DSMZ) under Accession No. DSM 33529, *Saccharomyces cerevisiae* deposited at DSMZ under Accession No. DSM 33527, and *Saccharomyces cerevisiae* deposited at DSMZ under Accession No. DSM 33528.

8. The method according to claim 1, wherein the microbial strain requires an exogenous source of heme for respiratory growth.

9. The method according to claim 1, wherein the microbial strain is a lactic acid bacteria strain.

10. The method according to claim 3, further comprising adding a cryoprotective agent to the microbial culture prior to freezing.

* * * * *